US009822347B2

(12) United States Patent
Giaccia et al.

(10) Patent No.: US 9,822,347 B2
(45) Date of Patent: *Nov. 21, 2017

(54) MODIFIED AXL PEPTIDES AND THEIR USE IN INHIBITION OF AXL SIGNALING IN ANTI-METASTATIC THERAPY

(71) Applicants: The Board of Trustees of the Leland Stanford Junior University, Stanford, CA (US); Aravive Biologics, Inc., Houston, TX (US)

(72) Inventors: Amato J. Giaccia, Stanford, CA (US); Erinn Bruno Rankin, Waltham, MA (US); Jennifer R. Cochran, Stanford, CA (US); Douglas Jones, Newton, MA (US); Mihalis Kariolis, Stanford, CA (US); Katherine Fuh, St. Louis, MO (US); Yu Miao, Sunnyvale, CA (US); Susan Hershenson, Palo Alto, CA (US)

(73) Assignees: The Board of Trustees of the Leland Stanford Junior University, Stanford, CA (US); Aravive Biologics, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/650,854

(22) PCT Filed: Dec. 12, 2013

(86) PCT No.: PCT/US2013/074786
§ 371 (c)(1),
(2) Date: Jun. 9, 2015

(87) PCT Pub. No.: WO2014/093690
PCT Pub. Date: Jun. 19, 2014

(65) Prior Publication Data
US 2015/0315553 A1 Nov. 5, 2015

Related U.S. Application Data

(60) Provisional application No. 61/737,276, filed on Dec. 14, 2012.

(51) Int. Cl.
*C12N 9/12* (2006.01)
*C07K 16/46* (2006.01)
*A61K 45/06* (2006.01)

(52) U.S. Cl.
CPC ............... *C12N 9/12* (2013.01); *A61K 45/06* (2013.01); *C07K 16/46* (2013.01); *C07K 2319/30* (2013.01); *C07K 2319/32* (2013.01); *C12Y 207/10001* (2013.01)

(58) Field of Classification Search
CPC .................... C07K 4/705; C07K 2319/30
See application file for complete search history.

(56) References Cited

U.S. PATENT DOCUMENTS

| 5,538,861 | A | 7/1996 | Schneider et al. | |
|---|---|---|---|---|
| 8,618,254 | B2 * | 12/2013 | Giaccia | C07K 14/705 530/350 |
| 9,074,192 | B2 | 7/2015 | Giaccia et al. | |
| 9,266,947 | B2 | 2/2016 | Giaccia et al. | |
| 2003/0017540 | A1 | 1/2003 | Baker et al. | |
| 2005/0186571 | A1 | 8/2005 | Ullrich et al. | |
| 2011/0014173 | A1 * | 1/2011 | Graham | C12N 9/1205 424/94.3 |
| 2011/0237498 | A1 * | 9/2011 | Raymond | C07K 14/4703 514/1.7 |
| 2015/0315552 | A1 | 11/2015 | Giaccia et al. | |
| 2015/0315553 | A1 | 11/2015 | Giaccia et al. | |
| 2016/0108378 | A1 * | 4/2016 | Giaccia | C12N 9/12 424/94.5 |
| 2016/0266136 | A1 * | 9/2016 | Cochran | G01N 33/574 |

FOREIGN PATENT DOCUMENTS

| JP | 2005-278631 A | 10/2005 |
|---|---|---|
| JP | 2005-532805 A | 11/2005 |
| WO | 2004/092735 A2 | 10/2004 |
| WO | 2004/108748 A2 | 12/2004 |
| WO | 2006058202 A2 | 6/2006 |
| WO | 2008/098139 A2 | 8/2008 |
| WO | 2009/005813 A1 | 1/2009 |
| WO | 2010/014755 A1 | 2/2010 |
| WO | 2010/130751 A1 | 11/2010 |
| WO | 2011/091305 A2 | 7/2011 |
| WO | 2014093690 A1 | 6/2014 |
| WO | 2014093707 A1 | 6/2014 |

OTHER PUBLICATIONS

Weidle et al., Cancer Genomics & Proteomics 2012; 9:357-72.*
Cherchia et al., Targeting Axl with an high-affinity inhibitory aptamer, Molecular Therapy, Dec. 2012, vol. 20, No. 12, pp. 2291-2303.
Healy et al., Gas 6 promotes Axl-mediated survival in pulmonary endothelial cells, Am J Physiol Lung Cell Mol Physiol, Jun. 2001, vol. 280, No. 6, pp. L1273-L1281.
Mark et al., Characterization of Gas6, a Member of the Superfamily of G domain-containing Proteins, as a Ligand for Rse and Axl., J Biol Chem. Apr. 19, 1996, vol. 271, No. 16, pp. 9785-9789.
Nagata et al., Identification of the product of growth arrest-specific gene 6 as a common ligand for Axl, Sky, and Mer receptor tyrosine kinases, J Biol Chem, Nov. 22, 1996, vol. 271, No. 47, pp. 30022-30027.
Sasaki et al., Structural basis for Gas6-Axl signalling, EMBO Journal, Jan. 11, 2006, vol. 25, No. 1, pp. 80-87.
Sawabu et al., "Growth Arrest-Specific Gene 6 and Axl Signaling Enhances Gastric Cancer Cell Survival via Akt Pathway", Molecular Carcinogenesis, 2007, pp. 155-164, vol. 46, Wiley, Hoboken, NJ.
Civan "Hepatic Fibrosis", 2006-2007, pp. 1-6, The Merck Manuals Online Medical Library, [online]. Whitehouse Station, NJ: Merck Research Laboratories, Retrieved from the Internet: < http://www.merckmanuals.com/professional/hepatic-and-biliarydisorders/fibrosis-and-cirrhosis/hepatic-fibrosis.
Balmana et al., "BRCA in breast cancer: ESMO Clinical Recommendations", Ann Oncol., 2009, pp. 19-20, 20 (supp 4):iv, Oxford University Press, Oxford, United Kingdom.
Tsou et al., "Receptor Tyrosine Kinases, TYRO3, AXL, and MER, Demonstrate Distinct Patterns and Complex Regulation of Ligand-induced Activation", The Journal of Biological Chemistry, 2014, 289(37): 25750-25763.

* cited by examiner

*Primary Examiner* — Jessica H Roark
(74) *Attorney, Agent, or Firm* — Pamela J. Sherwood; Bozicevic, Field & Francis LLP

(57) ABSTRACT

Compositions and methods are provided for alleviating cancer in a mammal by administering a therapeutic dose of a pharmaceutical composition that inhibits activity of AXL, MER or Tyro3 protein activity, for example by competitive or non-competitive inhibition of the binding interaction between AXL, MER or Tyro3 and its ligand GAS6.

3 Claims, 2 Drawing Sheets

```
                    SEQUENCE LISTING

<160> NUMBER OF SEQ ID NOS: 10

<210> SEQ ID NO 1
<211> LENGTH: 887
<212> TYPE: PRT
<213> ORGANISM: H. sapiens

<400> SEQUENCE: 1

Met Gly Arg Val Pro Leu Ala Trp Cys Leu Ala Leu Cys Gly Trp Ala
1               5                   10                  15

Cys Met Ala Pro Arg Gly Thr Gln Ala Glu Glu Ser Pro Phe Val Gly
            20                  25                  30

Asn Pro Gly Asn Ile Thr Gly Ala Arg Gly Leu Thr Gly Thr Leu Arg
        35                  40                  45

Cys Gln Leu Gln Val Gln Gly Glu Pro Pro Glu Val His Trp Leu Arg
    50                  55                  60

Asp Gly Gln Ile Leu Glu Leu Ala Asp Ser Thr Gln Thr Gln Val Pro
65                  70                  75                  80

Leu Gly Glu Asp Glu Gln Asp Asp Trp Ile Val Val Ser Gln Leu Arg
                85                  90                  95

Ile Thr Ser Leu Gln Leu Ser Asp Thr Gly Gln Tyr Gln Cys Leu Val
            100                 105                 110

Phe Leu Gly His Gln Thr Phe Val Ser Gln Pro Gly Tyr Val Gly Leu
        115                 120                 125
```

Glu Gly Leu Pro Tyr Phe Leu Glu Glu Pro Glu Asp Arg Thr Val Ala
    130                 135                 140

Ala Asn Thr Pro Phe Asn Leu Ser Cys Gln Ala Gln Gly Pro Pro Glu
145                 150                 155                 160

Pro Val Asp Leu Leu Trp Leu Gln Asp Ala Val Pro Leu Ala Thr Ala
                165                 170                 175

Pro Gly His Gly Pro Gln Arg Ser Leu His Val Pro Gly Leu Asn Lys
            180                 185                 190

Thr Ser Ser Phe Ser Cys Glu Ala His Asn Ala Lys Gly Val Thr Thr
        195                 200                 205

Ser Arg Thr Ala Thr Ile Thr Val Leu Pro Gln Gln Pro Arg Asn Leu
210                 215                 220

His Leu Val Ser Arg Gln Pro Thr Glu Leu Glu Val Ala Trp Thr Pro
225                 230                 235                 240

Gly Leu Ser Gly Ile Tyr Pro Leu Thr His Cys Thr Leu Gln Ala Val
                245                 250                 255

Leu Ser Asn Asp Gly Met Gly Ile Gln Ala Gly Glu Pro Asp Pro Pro
            260                 265                 270

Glu Glu Pro Leu Thr Ser Gln Ala Ser Val Pro Pro His Gln Leu Arg
        275                 280                 285

Leu Gly Ser Leu His Pro His Thr Pro Tyr His Ile Arg Val Ala Cys
290                 295                 300

Thr Ser Ser Gln Gly Pro Ser Ser Trp Thr His Trp Leu Pro Val Glu
305                 310                 315                 320

Thr Pro Glu Gly Val Pro Leu Gly Pro Pro Glu Asn Ile Ser Ala Thr
                325                 330                 335

Arg Asn Gly Ser Gln Ala Phe Val His Trp Gln Glu Pro Arg Ala Pro
            340                 345                 350

Leu Gln Gly Thr Leu Leu Gly Tyr Arg Leu Ala Tyr Gln Gly Gln Asp
        355                 360                 365

Thr Pro Glu Val Leu Met Asp Ile Gly Leu Arg Gln Glu Val Thr Leu
370                 375                 380

Glu Leu Gln Gly Asp Gly Ser Val Ser Asn Leu Thr Val Cys Val Ala
385                 390                 395                 400

Ala Tyr Thr Ala Ala Gly Asp Gly Pro Trp Ser Leu Pro Val Pro Leu
                405                 410                 415

Glu Ala Trp Arg Pro Gly Gln Ala Gln Pro Val His Gln Leu Val Lys
            420                 425                 430

Glu Pro Ser Thr Pro Ala Phe Ser Trp Pro Trp Trp Tyr Val Leu Leu
        435                 440                 445

Gly Ala Val Val Ala Ala Ala Cys Val Leu Ile Leu Ala Leu Phe Leu
450                 455                 460

Val His Arg Arg Lys Lys Glu Thr Arg Tyr Gly Glu Val Phe Glu Pro
465                 470                 475                 480

Thr Val Glu Arg Gly Glu Leu Val Val Arg Tyr Arg Val Arg Lys Ser
                485                 490                 495

Tyr Ser Arg Arg Thr Thr Glu Ala Thr Leu Asn Ser Leu Gly Ile Ser
            500                 505                 510

Glu Glu Leu Lys Glu Lys Leu Arg Asp Val Met Val Asp Arg His Lys
        515                 520                 525

Val Ala Leu Gly Lys Thr Leu Gly Glu Gly Glu Phe Gly Ala Val Met
530                 535                 540

Glu Gly Gln Leu Asn Gln Asp Asp Ser Ile Leu Lys Val Ala Val Lys

```
                545                 550                 555                 560
Thr Met Lys Ile Ala Ile Cys Thr Arg Ser Glu Leu Glu Asp Phe Leu
                    565                 570                 575
Ser Glu Ala Val Cys Met Lys Glu Phe Asp His Pro Asn Val Met Arg
                580                 585                 590
Leu Ile Gly Val Cys Phe Gln Gly Ser Glu Arg Glu Ser Phe Pro Ala
            595                 600                 605
Pro Val Val Ile Leu Pro Phe Met Lys His Gly Asp Leu His Ser Phe
        610                 615                 620
Leu Leu Tyr Ser Arg Leu Gly Asp Gln Pro Val Tyr Leu Pro Thr Gln
625                 630                 635                 640
Met Leu Val Lys Phe Met Ala Asp Ile Ala Ser Gly Met Glu Tyr Leu
                    645                 650                 655
Ser Thr Lys Arg Phe Ile His Arg Asp Leu Ala Ala Arg Asn Cys Met
                660                 665                 670
Leu Asn Glu Asn Met Ser Val Cys Val Ala Asp Phe Gly Leu Ser Lys
            675                 680                 685
Lys Ile Tyr Asn Gly Asp Tyr Tyr Arg Gln Gly Arg Ile Ala Lys Met
        690                 695                 700
Pro Val Lys Trp Ile Ala Ile Glu Ser Leu Ala Asp Arg Val Tyr Thr
705                 710                 715                 720
Ser Lys Ser Asp Val Trp Ser Phe Gly Val Thr Met Trp Glu Ile Ala
                    725                 730                 735
Thr Arg Gly Gln Thr Pro Tyr Pro Gly Val Glu Asn Ser Glu Ile Tyr
                740                 745                 750
Asp Tyr Leu Arg Gln Gly Asn Arg Leu Lys Gln Pro Ala Asp Cys Leu
            755                 760                 765
Asp Gly Leu Tyr Ala Leu Met Ser Arg Cys Trp Glu Leu Asn Pro Gln
        770                 775                 780
Asp Arg Pro Ser Phe Thr Glu Leu Arg Glu Asp Leu Glu Asn Thr Leu
785                 790                 795                 800
Lys Ala Leu Pro Pro Ala Gln Glu Pro Asp Glu Ile Leu Tyr Val Asn
                    805                 810                 815
Met Asp Glu Gly Gly Gly Tyr Pro Glu Pro Pro Gly Ala Ala Gly Gly
                820                 825                 830
Ala Asp Pro Pro Thr Gln Pro Asp Pro Lys Asp Ser Cys Ser Cys Leu
            835                 840                 845
Thr Ala Ala Glu Val His Pro Ala Gly Arg Tyr Val Leu Cys Pro Ser
        850                 855                 860
Thr Thr Pro Ser Pro Ala Gln Pro Ala Asp Arg Gly Ser Pro Ala Ala
865                 870                 875                 880
Pro Gly Gln Glu Asp Gly Ala
                885

<210> SEQ ID NO 2
<211> LENGTH: 999
<212> TYPE: PRT
<213> ORGANISM: H. sapiens

<400> SEQUENCE: 2

Met Gly Pro Ala Pro Leu Pro Leu Leu Leu Gly Leu Phe Leu Pro Ala
 1               5                  10                  15
Leu Trp Arg Arg Ala Ile Thr Glu Ala Arg Glu Glu Ala Lys Pro Tyr
                20                  25                  30
```

-continued

Pro Leu Phe Pro Gly Pro Phe Pro Gly Ser Leu Gln Thr Asp His Thr
             35                  40                  45

Pro Leu Leu Ser Leu Pro His Ala Ser Gly Tyr Gln Pro Ala Leu Met
 50                  55                  60

Phe Ser Pro Thr Gln Pro Gly Arg Pro His Thr Gly Asn Val Ala Ile
 65                  70                  75                  80

Pro Gln Val Thr Ser Val Glu Ser Lys Pro Leu Pro Leu Ala Phe
                 85                  90                  95

Lys His Thr Val Gly His Ile Ile Leu Ser Glu His Lys Gly Val Lys
                100                 105                 110

Phe Asn Cys Ser Ile Ser Val Pro Asn Ile Tyr Gln Asp Thr Thr Ile
            115                 120                 125

Ser Trp Trp Lys Asp Gly Lys Glu Leu Leu Gly Ala His His Ala Ile
    130                 135                 140

Thr Gln Phe Tyr Pro Asp Asp Glu Val Thr Ala Ile Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
            180                 185                 190

Val Gln Gly Leu Pro His Phe Thr Lys Gln Pro Glu Ser Met Asn Val
    195                 200                 205

Thr Arg Asn Thr Ala Phe Asn Leu Thr Cys Gln Ala Val Gly Pro Pro
    210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
    275                 280                 285

Glu Val Ser Ile Arg Asn Ser Thr Ala His Ser Ile Leu Ile Ser Trp
290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335

Thr Ser Ala Leu Pro His Leu Tyr Gln Ile Lys Gln Leu Gln Ala Leu
            340                 345                 350

Ala Asn Tyr Ser Ile Gly Val Ser Cys Met Asn Glu Ile Gly Trp Ser
    355                 360                 365

Ala Val Ser Pro Trp Ile Leu Ala Ser Thr Thr Glu Gly Ala Pro Ser
    370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
            420                 425                 430

Lys Glu Leu Leu Glu Glu Val Gly Gln Asn Gly Ser Arg Ala Arg Ile
    435                 440                 445

Ser Val Gln Val His Asn Ala Thr Cys Thr Val Arg Ile Ala Ala Val

-continued

```
                450             455             460
Thr Arg Gly Gly Val Gly Pro Phe Ser Asp Pro Val Lys Ile Phe Ile
465             470             475             480

Pro Ala His Gly Trp Val Asp Tyr Ala Pro Ser Ser Thr Pro Ala Pro
                485             490             495

Gly Asn Ala Asp Pro Val Leu Ile Ile Phe Gly Cys Phe Cys Gly Phe
                500             505             510

Ile Leu Ile Gly Leu Ile Leu Tyr Ile Ser Leu Ala Ile Arg Lys Arg
                515             520             525

Val Gln Glu Thr Lys Phe Gly Asn Ala Phe Thr Glu Glu Asp Ser Glu
            530             535             540

Leu Val Val Asn Tyr Ile Ala Lys Lys Ser Phe Cys Arg Arg Ala Ile
545             550             555             560

Glu Leu Thr Leu His Ser Leu Gly Val Ser Glu Glu Leu Gln Asn Lys
                565             570             575

Leu Glu Asp Val Val Ile Asp Arg Asn Leu Leu Ile Leu Gly Lys Ile
                580             585             590

Leu Gly Glu Gly Glu Phe Gly Ser Val Met Glu Gly Asn Leu Lys Gln
            595             600             605

Glu Asp Gly Thr Ser Leu Lys Val Ala Val Lys Thr Met Lys Leu Asp
610             615             620

Asn Ser Ser Gln Arg Glu Ile Glu Glu Phe Leu Ser Glu Ala Ala Cys
625             630             635             640

Met Lys Asp Phe Ser His Pro Asn Val Ile Arg Leu Leu Gly Val Cys
                645             650             655

Ile Glu Met Ser Ser Gln Gly Ile Pro Lys Pro Met Val Ile Leu Pro
                660             665             670

Phe Met Lys Tyr Gly Asp Leu His Thr Tyr Leu Leu Tyr Ser Arg Leu
            675             680             685

Glu Thr Gly Pro Lys His Ile Pro Leu Gln Thr Leu Leu Lys Phe Met
            690             695             700

Val Asp Ile Ala Leu Gly Met Glu Tyr Leu Ser Asn Arg Asn Phe Leu
705             710             715             720

His Arg Asp Leu Ala Ala Arg Asn Cys Met Leu Arg Asp Asp Met Thr
                725             730             735

Val Cys Val Ala Asp Phe Gly Leu Ser Lys Lys Ile Tyr Ser Gly Asp
                740             745             750

Tyr Tyr Arg Gln Gly Arg Ile Ala Lys Met Pro Val Lys Trp Ile Ala
            755             760             765

Ile Glu Ser Leu Ala Asp Arg Val Tyr Thr Ser Lys Ser Asp Val Trp
770             775             780

Ala Phe Gly Val Thr Met Trp Glu Ile Ala Thr Arg Gly Met Thr Pro
785             790             795             800

Tyr Pro Gly Val Gln Asn His Glu Met Tyr Asp Tyr Leu Leu His Gly
                805             810             815

His Arg Leu Lys Gln Pro Glu Asp Cys Leu Asp Glu Leu Tyr Glu Ile
                820             825             830

Met Tyr Ser Cys Trp Arg Thr Asp Pro Leu Asp Arg Pro Thr Phe Ser
            835             840             845

Val Leu Arg Leu Gln Leu Glu Lys Leu Leu Glu Ser Leu Pro Asp Val
            850             855             860

Arg Asn Gln Ala Asp Val Ile Tyr Val Asn Thr Gln Leu Leu Glu Ser
865             870             875             880
```

```
Ser Glu Gly Leu Ala Gln Gly Ser Thr Leu Ala Pro Leu Asp Leu Asn
            885                 890                 895

Ile Asp Pro Asp Ser Ile Ile Ala Ser Cys Thr Pro Arg Ala Ala Ile
            900                 905                 910

Ser Val Val Thr Ala Glu Val His Asp Ser Lys Pro His Glu Gly Arg
            915                 920                 925

Tyr Ile Leu Asn Gly Gly Ser Glu Glu Trp Glu Asp Leu Thr Ser Ala
        930                 935                 940

Pro Ser Ala Ala Val Thr Ala Glu Lys Asn Ser Val Leu Pro Gly Glu
945                 950                 955                 960

Arg Leu Val Arg Asn Gly Val Ser Trp Ser His Ser Ser Met Leu Pro
                965                 970                 975

Leu Gly Ser Ser Leu Pro Asp Glu Leu Leu Phe Ala Asp Asp Ser Ser
            980                 985                 990

Glu Gly Ser Glu Val Leu Met
            995

<210> SEQ ID NO 3
<211> LENGTH: 890
<212> TYPE: PRT
<213> ORGANISM: H. sapiens

<400> SEQUENCE: 3

Met Ala Leu Arg Arg Ser Met Gly Arg Pro Gly Leu Pro Pro Leu Pro
 1               5                  10                  15

Leu Pro Pro Pro Arg Leu Gly Leu Leu Ala Leu Ala Leu Ala Leu Ala Ser
            20                  25                  30

Leu Leu Leu Pro Glu Ser Ala Ala Ala Gly Leu Lys Leu Met Gly Ala
        35                  40                  45

Pro Val Lys Leu Thr Val Ser Gln Gly Gln Pro Val Lys Leu Asn Cys
50                  55                  60

Ser Val Glu Gly Met Glu Glu Pro Asp Ile Gln Trp Val Lys Asp Gly
65                  70                  75                  80

Ala Val Val Gln Asn Leu Asp Gln Leu Tyr Ile Pro Val Ser Glu Gln
                85                  90                  95

His Trp Ile Gly Phe Leu Ser Leu Lys Ser Val Glu Arg Ser Asp Ala
            100                 105                 110

Gly Arg Tyr Trp Cys Gln Val Glu Asp Gly Gly Glu Thr Glu Ile Ser
        115                 120                 125

Gln Pro Val Trp Leu Thr Val Glu Gly Val Pro Phe Phe Thr Val Glu
    130                 135                 140

Pro Lys Asp Leu Ala Val Pro Pro Asn Ala Pro Phe Gln Leu Ser Cys
145                 150                 155                 160

Glu Ala Val Gly Pro Pro Glu Pro Val Thr Ile Val Trp Trp Arg Gly
                165                 170                 175

Thr Thr Lys Ile Gly Gly Pro Ala Pro Ser Pro Ser Val Leu Asn Val
            180                 185                 190

Thr Gly Val Thr Gln Ser Thr Met Phe Ser Cys Glu Ala His Asn Leu
        195                 200                 205

Lys Gly Leu Ala Ser Ser Arg Thr Ala Thr Val His Leu Gln Ala Leu
    210                 215                 220

Pro Ala Ala Pro Phe Asn Ile Thr Val Thr Lys Leu Ser Ser Ser Asn
225                 230                 235                 240

Ala Ser Val Ala Trp Met Pro Gly Ala Asp Gly Arg Ala Leu Leu Gln
```

```
            245                 250                 255
Ser Cys Thr Val Gln Val Thr Gln Ala Pro Gly Gly Trp Glu Val Leu
            260                 265                 270

Ala Val Val Pro Val Pro Pro Phe Thr Cys Leu Leu Arg Asp Leu
            275                 280             285

Val Pro Ala Thr Asn Tyr Ser Leu Arg Val Arg Cys Ala Asn Ala Leu
            290                 295             300

Gly Pro Ser Pro Tyr Ala Asp Trp Val Pro Phe Gln Thr Lys Gly Leu
305                 310                 315                 320

Ala Pro Ala Ser Ala Pro Gln Asn Leu His Ala Ile Arg Thr Asp Ser
                325                 330                 335

Gly Leu Ile Leu Glu Trp Glu Val Ile Pro Glu Ala Pro Leu Glu
            340                 345                 350

Gly Pro Leu Gly Pro Tyr Lys Leu Ser Trp Val Gln Asp Asn Gly Thr
            355                 360                 365

Gln Asp Glu Leu Thr Val Glu Gly Thr Arg Ala Asn Leu Thr Gly Trp
370                 375                 380

Asp Pro Gln Lys Asp Leu Ile Val Arg Val Cys Val Ser Asn Ala Val
385                 390                 395                 400

Gly Cys Gly Pro Trp Ser Gln Pro Leu Val Val Ser Ser His Asp Arg
                405                 410                 415

Ala Gly Gln Gln Gly Pro Pro His Ser Arg Thr Ser Trp Val Pro Val
                420                 425                 430

Val Leu Gly Val Leu Thr Ala Leu Val Thr Ala Ala Ala Leu Ala Leu
            435                 440                 445

Ile Leu Leu Arg Lys Arg Arg Lys Glu Thr Arg Phe Gly Gln Ala Phe
            450                 455                 460

Asp Ser Val Met Ala Arg Gly Glu Pro Ala Val His Phe Arg Ala Ala
465                 470                 475                 480

Arg Ser Phe Asn Arg Glu Arg Pro Glu Arg Ile Glu Ala Thr Leu Asp
                485                 490                 495

Ser Leu Gly Ile Ser Asp Glu Leu Lys Glu Lys Leu Glu Asp Val Leu
                500                 505                 510

Ile Pro Glu Gln Gln Phe Thr Leu Gly Arg Met Leu Gly Lys Gly Glu
            515                 520                 525

Phe Gly Ser Val Arg Glu Ala Gln Leu Lys Gln Glu Asp Gly Ser Phe
            530                 535                 540

Val Lys Val Ala Val Lys Met Leu Lys Ala Asp Ile Ile Ala Ser Ser
545                 550                 555                 560

Asp Ile Glu Glu Phe Leu Arg Glu Ala Ala Cys Met Lys Glu Phe Asp
                565                 570                 575

His Pro His Val Ala Lys Leu Val Gly Val Ser Leu Arg Ser Arg Ala
                580                 585                 590

Lys Gly Arg Leu Pro Ile Pro Met Val Ile Leu Pro Phe Met Lys His
            595                 600                 605

Gly Asp Leu His Ala Phe Leu Leu Ala Ser Arg Ile Gly Glu Asn Pro
            610                 615                 620

Phe Asn Leu Pro Leu Gln Thr Leu Ile Arg Phe Met Val Asp Ile Ala
625                 630                 635                 640

Cys Gly Met Glu Tyr Leu Ser Ser Arg Asn Phe Ile His Arg Asp Leu
                645                 650                 655

Ala Ala Arg Asn Cys Met Leu Ala Glu Asp Met Thr Val Cys Val Ala
                660                 665                 670
```

```
Asp Phe Gly Leu Ser Arg Lys Ile Tyr Ser Gly Asp Tyr Tyr Arg Gln
        675                 680                 685

Gly Cys Ala Ser Lys Leu Pro Val Lys Trp Leu Ala Leu Glu Ser Leu
        690                 695                 700

Ala Asp Asn Leu Tyr Thr Val Gln Ser Asp Val Trp Ala Phe Gly Val
705                 710                 715                 720

Thr Met Trp Glu Ile Met Thr Arg Gly Gln Thr Pro Tyr Ala Gly Ile
                725                 730                 735

Glu Asn Ala Glu Ile Tyr Asn Tyr Leu Ile Gly Gly Asn Arg Leu Lys
                740                 745                 750

Gln Pro Pro Glu Cys Met Glu Asp Val Tyr Asp Leu Met Tyr Gln Cys
                755                 760                 765

Trp Ser Ala Asp Pro Lys Gln Arg Pro Ser Phe Thr Cys Leu Arg Met
        770                 775                 780

Glu Leu Glu Asn Ile Leu Gly Gln Leu Ser Val Leu Ser Ala Ser Gln
785                 790                 795                 800

Asp Pro Leu Tyr Ile Asn Ile Glu Arg Ala Glu Pro Thr Ala Gly
                805                 810                 815

Gly Ser Leu Glu Leu Pro Gly Arg Asp Gln Pro Tyr Ser Gly Ala Gly
        820                 825                 830

Asp Gly Ser Gly Met Gly Ala Val Gly Gly Thr Pro Ser Asp Cys Arg
        835                 840                 845

Tyr Ile Leu Thr Pro Gly Gly Leu Ala Glu Gln Pro Gly Gln Ala Glu
        850                 855                 860

His Gln Pro Glu Ser Pro Leu Asn Glu Thr Gln Arg Leu Leu Leu Leu
865                 870                 875                 880

Gln Gln Gly Leu Leu Pro His Ser Ser Cys
                885                 890

<210> SEQ ID NO 4
<211> LENGTH: 20
<212> TYPE: PRT
<213> ORGANISM: H. sapiens

<400> SEQUENCE: 4

Leu Arg Met Phe Ser Gly Thr Pro Val Ile Arg Leu Arg Phe Lys Arg
1               5                   10                  15

Leu Gln Pro Thr
            20

<210> SEQ ID NO 5
<211> LENGTH: 10
<212> TYPE: PRT
<213> ORGANISM: H. sapiens

<400> SEQUENCE: 5

Glu Val Gly Arg Val Thr Ser Ser Gly Pro
1               5                   10

<210> SEQ ID NO 6
<211> LENGTH: 8
<212> TYPE: PRT
<213> ORGANISM: H. sapiens

<400> SEQUENCE: 6

Arg Asn Leu Val Ile Lys Val Asn
1               5
```

```
<210> SEQ ID NO 7
<211> LENGTH: 9
<212> TYPE: PRT
<213> ORGANISM: H. sapiens

<400> SEQUENCE: 7

Asp Ala Val Met Lys Ile Ala Val Ala
 1               5

<210> SEQ ID NO 8
<211> LENGTH: 16
<212> TYPE: PRT
<213> ORGANISM: H. sapiens

<400> SEQUENCE: 8

Glu Arg Gly Leu Tyr His Leu Asn Leu Thr Val Gly Ile Pro Phe His
 1               5                  10                  15

<210> SEQ ID NO 9
<211> LENGTH: 17
<212> TYPE: PRT
<213> ORGANISM: H. sapiens

<400> SEQUENCE: 9

Trp Leu Asn Gly Glu Asp Thr Thr Ile Gln Glu Thr Val Val Asn Arg
 1               5                  10                  15

Met

<210> SEQ ID NO 10
<211> LENGTH: 5
<212> TYPE: PRT
<213> ORGANISM: Artificial Sequence
<220> FEATURE:
<223> OTHER INFORMATION: Synthetic Linker

<400> SEQUENCE: 10

Gly Gly Gly Gly Ser
 1               5
```

MODIFIED AXL PEPTIDES AND THEIR USE IN INHIBITION OF AXL SIGNALING IN ANTI-METASTATIC THERAPY

FIELD OF THE INVENTION

The present invention relates to tumor invasion and metastasis, e.g., treatments or diagnoses of tumor invasion or metastasis via pathways related to AXL, MER and Tyro3 and/or GAS6.

BACKGROUND OF THE INVENTION

Invasion and metastasis are the most insidious and life-threatening aspects of cancer. While tumors with minimal or no invasion may be successfully removed, once the neoplasm becomes invasive, it can disseminate via the lymphatics and/or vascular channels to multiple sites, and complete removal becomes very difficult. Invasion and metastases kill hosts through two processes: local invasion and distant organ colonization and injury. Local invasion can compromise the function of involved tissues by local compression, local destruction, or prevention of normal organ function. The most significant turning point in cancer, however, is the establishment of distant metastasis. The patient can no longer be cured by local therapy alone at this point.

The process of metastasis is a cascade of linked sequential steps involving multiple host-tumor interactions. This complex process requires the cells to enter into the vascular or lymphatic circulation, arrest at a distant vascular or lymphatic bed, actively extravasate into the organ interstitium and parenchyma, and proliferate as a secondary colony. Metastatic potential is influenced by the local microenvironment, angiogenesis, stroma-tumor interactions, elaboration of cytokines by the local tissue, and by the molecular phenotype of the tumor and host cells.

Local microinvasion can occur early, even though distant dissemination may not be evident or may not yet have begun. Tumor cells penetrate the epithelial basement membrane and enter the underlying interstitial stroma during the transition from in situ to invasive carcinoma. Once the tumor cells invade the underlying stroma, they gain access to the lymphatics and blood vessels for distant dissemination while releasing matrix fragments and growth factors. General and widespread changes occur in the organization, distribution, and quantity of the epithelial basement membrane during the transition from benign to invasive carcinoma.

Therapeutic efforts in cancer prevention and treatment are being focused at the level of signaling pathways or selective modulatory proteins. Protein kinase activities, calcium homeostasis, and oncoprotein activation are driving signals and therefore may be key regulatory sites for therapeutic intervention. Kinases in signaling pathways regulating invasion and angiogenesis may be important regulators of metastasis. One of the largest classes of biochemical molecular targets is the family of receptor tyrosine kinases (RTKs). The most common receptor tyrosine kinase molecular targets to date are the EGF and vascular endothelial growth factor (VEGF) receptors. Newer kinase molecular targets include the type III RTK family of c-kit, and abl. Inhibitors of these molecules have been administered in combination with classic chemotherapeutics.

Metastases ultimately are responsible for much of the suffering and mortality from cancer. A need exists to identify and target molecular and functional markers that identify metastatic cancer cells and to generate reagents for their specific inhibition.

Publications in this field include, inter alia, Li et al. Oncogene. (2009) 28(39):3442-55; United States Patent Application, 20050186571 by Ullrich et al.; United States Patent Application 20080293733 by Bearss et al.; Sun et al. Oncology. 2004; 66(6):450-7; Gustafsson et al. Clin Cancer Res. (2009) 15(14):4742-9; Wimmel et al. Eur J Cancer. 2001 37(17):2264-74; Koorstra et al. Cancer Biol Ther. 2009 8(7):618-26; Tai et al. Oncogene. (2008) 27(29):4044-55

The receptor tyrosine kinase AXL (also known as Ufo and Tyro7) belongs to a family of tyrosine receptors that includes Tyro3 (Sky) and Mer (Tyro12). A common ligand for AXL family is GAS6 (Growth arrest-specific protein 6). Human AXL is a 2,682-bp open reading frame capable of directing the synthesis of an 894-amino acid polypeptide. Two variant mRNAs have been characterized, transcript variant 1 may be accessed at Genbank, NM_021913.3 and transcript variant 2 may be accessed at NM_001699.4. The polypeptide sequence of the native protein is provided as SEQ ID NO:1, and specific reference may be made to the sequence with respect to amino acid modifications. Important cellular functions of GAS6/AXL include cell adhesion, migration, phagocytosis, and inhibition of apoptosis. GAS6 and AXL family receptors are highly regulated in a tissue and disease specific manner.

AXL, MER and Tyro3 are each characterized by a unique molecular structure, in that the intracellular region has the typical structure of a receptor tyrosine kinase and the extracellular domain contains fibronectin III and Ig motifs similar to cadherin-type adhesion molecules. During development, AXL, MER and Tyro3 are expressed in various organs, including the brain, suggesting that this RTK is involved in mesenchymal and neural development. In the adult, AXL, MER and Tyro3 expression is low but returns to high expression levels in a variety of tumors. GAS6 is, so far, the single, activating ligand for AXL, MER and Tyro3.

Receptor tyrosine kinases (RTK) are generally activated by ligands that promote receptor dimerization and, in turn, autophosphorylation of tyrosine residues within the cytosolic domain. Binding of signaling proteins to these phosphorylated tyrosine residues then leads to downstream signaling. AXL, MER and Tyro3 family of RTKs are unique in that they are activated by GAS6, members of the vitamin K-dependent protein family that resembles blood coagulation factors rather than typical growth factors.

SUMMARY OF THE INVENTION

The present invention is based in part on the discovery that AXL, MER and Tyro3 and/or GAS6 related pathways are related to tumor invasion and/or metastasis. Accordingly, the present invention provides compositions and methods useful for treating tumor invasion and/or metastasis, e.g., via inhibition of AXL, MER and/or Tyro3 and/or GAS6 related pathways. In addition, the present invention provides reagents and methods useful for determining the susceptibility or likelihood of a tumor to become invasive and/or metastatic, e.g., via detecting the level of activity of AXL, MER, Tyro3 and/or GAS6.

In some embodiments, the agent useful for treating tumor invasion and/or metastasis, e.g., via inhibition of AXL, MER and Tyro3 and/or GAS6 related pathways is an inhibitor agent. In some embodiments, the inhibitor agent is selected from the group consisting of (a) an inhibitor of AXL, MER and/or Tyro3 activity, (b) an inhibitor of GAS6 activity and (c) and inhibitor of AXL, MER and/or Tyro3-GAS6 interaction, wherein the inhibitor agent is capable of binding to GAS6 with increased affinity compared to wild-type AXL, MER or Tyro3.

In some embodiments, the inhibitor agent binds to two or more epitopes on a single GAS6.

In some embodiments, at least one of the epitopes is the major or minor AXL, MER or Tyro3 binding site on GAS6.

In some embodiments, the inhibitor agent is capable of binding to the major and minor AXL, MER or Tyro3 binding sites on a single GAS6.

In some embodiments, the inhibitor agent is capable of binding to the major AXL, MER or Tyro3 binding site of GAS6 and one or more additional GAS6 epitopes on a single GAS6.

In some embodiments, the inhibitor agent is capable of binding to the minor AXL, MER or Tyro3 binding site on GAS6 and one or more additional epitopes on a single GAS6.

In some embodiments, the inhibitor agent is capable of binding two or more epitopes on a single GAS6.

In some embodiments, the inhibitor agent is capable of antagonizing the major and/or minor GAS6/receptor binding interaction, where the receptor is selected from AXL, MER and Tyro3.

In some embodiments, the inhibitor agent is capable of antagonizing the major GAS6/receptor binding interaction, where the receptor is selected from AXL, MER and Tyro3.

In some embodiments, the inhibitor agent is capable of antagonizing the minor GAS6/receptor binding interaction, where the receptor is selected from AXL, MER and Tyro3.

In some embodiments, the inhibitor agent is a polypeptide, a polypeptide-carrier fusion, a polypeptide-Fc fusion, a polypeptide-conjugate, a polypeptide-drug conjugate, an antibody, a bispecific antibody, an antibody drug conjugate, an antibody fragment, an antibody-related structure, or a combination thereof.

In some embodiments, the inhibitor agent is a natural or synthetic polypeptide.

In some embodiments, the inhibitor agent is a non-antibody polypeptide.

In some embodiments, the inhibitor agent of the present invention can include, for example but is not limited to a darpin, an avimer, an adnectin, an anticalin, an affibody, a maxibody, or other protein structural scaffold, or a combination thereof.

In some embodiments, the inhibitor agent is a polypeptide-conjugate or antibody-conjugate.

In some embodiments, the inhibitor agent is a polypeptide-polymer conjugate, where the polymer is selected from PEG, PEG-containing polymers, degradable polymers, biocompatible polymers, hydrogels, and other polymer structures or a combination thereof.

In some embodiments, the inhibitor agent is a polypeptide, wherein said polypeptide comprises a soluble AXL variant polypeptide wherein said AXL variant polypeptide lacks the AXL transmembrane domain and has at least one mutation relative to wild-type that increases affinity of the AXL polypeptide binding to GAS6.

In some embodiments, the inhibitor agent is a polypeptide, wherein said polypeptide comprises a soluble MER variant polypeptide wherein said MER variant polypeptide lacks the MER transmembrane domain and has at least one mutation relative to wild-type that increases affinity of the MER polypeptide binding to GAS6.

In some embodiments, the inhibitor agent is a polypeptide, wherein said polypeptide comprises a soluble Tyro3 variant polypeptide wherein said Tyro3 variant polypeptide lacks the Tyro3 transmembrane domain and has at least one mutation relative to wild-type that increases affinity of the Tyro3 polypeptide binding to GAS6.

In some embodiments, the inhibitor is an AXL, MER or Tyro3 variant polypeptide that inhibits binding between a wild-type AXL, MER and/or Tyro3 polypeptide and a GAS6 protein in vivo or in vitro.

In some embodiments, the polypeptide lacks a functional fibronectin (FN) domain and/or exhibits increased affinity of the AXL, MER or Tyro3 variant polypeptide binding to GAS6 compared to wild-type AXL, MER or Tyro3.

In some embodiments, the AXL, MER or Tyro3 variant polypeptide lacks the transmembrane domain, has more than one Ig1 domain and exhibits increased affinity of the AXL, MER or Tyro3 variant polypeptide binding to GAS6 as compared to wild-type AXL, MER or Tyro3.

In some embodiments, the AXL, MER or Tyro3 variant polypeptide has two Ig1 domains. In some embodiments, the polypeptide has three Ig1 domains.

In some embodiments, the AXL, MER or Tyro3 polypeptide lacks the transmembrane domain, has more than one Ig2 domain and exhibits increased affinity of the AXL, MER or Tyro3 polypeptide binding to GAS6 as compared to wild-type AXL, MER or Tyro3.

In some embodiments, the AXL, MER or Tyro3 variant polypeptide has two Ig2 domains.

In some embodiments, the polypeptide is a soluble AXL, MER or Tyro3 variant polypeptide, wherein said soluble AXL variant polypeptide lacks the AXL, MER or Tyro3 transmembrane domain, has more than one Ig1 domain, more than one Ig2 domain and exhibits increased affinity of the AXL, MER or Tyro3 variant polypeptide binding to GAS6 as compared to wild-type AXL, MER or Tyro3.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has more than one Ig1 domain, more than one Ig2 domain, and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the soluble AXL, MER or Tyro3 variant polypeptide has two Ig1 domains and two Ig2 domains.

In some embodiments, the soluble AXL, MER or Tyro3 variant polypeptide has the immunoglobulin domains connected directly.

In some embodiments, the soluble AXL, MER or Tyro3 variant polypeptide has the immunoglobulin domains connected indirectly.

In some embodiments, the soluble AXL, MER or Tyro3 variant polypeptide lacks the AXL, MER or Tyro3 transmembrane domain, is capable of binding both the major and minor binding site of a single GAS6 and wherein said AXL, MER or Tyro3 variant polypeptide exhibits increased affinity of the AXL, MER or Tyro3 polypeptide binding to GAS6 as compared to wild-type AXL, MER or Tyro3.

In some embodiments, the polypeptide has one Ig1 domain and lacks a functional Ig2 domain.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

In some embodiments, the AXL, MER or Tyro3 variant polypeptide is a fusion protein comprising an Fc domain.

In some embodiments, the AXL, MER or Tyro3 variant polypeptide further comprises a linker. In some embodiments, the linker comprises one or more (GLY)$_4$SER units.

In some embodiments, the AXL, MER or Tyro3 variant polypeptide lacks the AXL, MER or Tyro3 intracellular domain.

In some embodiments, the AXL, MER or Tyro3 variant polypeptide lacks a functional fibronectin (FN) domain and wherein said AXL, MER or Tyro3 variant polypeptide exhibits increased affinity of the polypeptide binding to GAS6 as compared to wild-type AXL, MER or Tyro3.

In some embodiments, the AXL, MER or Tyro3 variant polypeptide comprises at least one amino acid modification relative to the wild-type AXL, MER or Tyro3 sequence.

In some embodiments, the soluble AXL variant polypeptide comprises at least one amino acid modification within a region selected from the group consisting of 1) between 15-50, 2) between 60-120, and 3) between 125-135 of the wild-type AXL sequence (SEQ ID NO:1).

In some embodiments, the soluble AXL variant polypeptide comprises at least one amino acid modification at position 19, 23, 26, 27, 32, 33, 38, 44, 61, 65, 72, 74, 78, 79, 86, 87, 88, 90, 92, 97, 98, 105, 109, 112, 113, 116, 118, or 127 of the wild-type AXL sequence (SEQ ID NO: 1) or a combination thereof.

In some embodiments, the soluble AXL variant polypeptide comprises at least one amino acid modification selected from the group consisting of 1) A19T, 2) T23M, 3) E26G, 4) E27G or E27K 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) G129E and a combination thereof.

In some embodiments, the soluble AXL variant polypeptide comprises amino acid changes relative to the wild-type AXL sequence (SEQ ID NO: 1) at the following positions: (a) glycine 32; (b) aspartic acid 87; (c) valine 92; and (d) glycine 127.

In some embodiments, the soluble AXL variant polypeptide comprises amino acid changes relative to the wild-type AXL sequence (SEQ ID NO: 1) at the following positions: (a) aspartic acid 87 and (b) valine 92.

In some embodiments, the soluble AXL variant polypeptide comprises amino acid changes relative to the wild-type AXL sequence (SEQ ID NO: 1) at the following positions: (a) glycine 32; (b) aspartic acid 87; (c) valine 92; (d) glycine 127 and (e) alanine 72.

In some embodiments, the soluble AXL variant polypeptide comprises amino acid changes relative to the wild-type AXL sequence (SEQ ID NO: 1) at the following position: alanine 72.

In some embodiments, in the soluble AXL variant polypeptide the glycine 32 residue is replaced with a serine residue, aspartic acid 87 residue is replaced with a glycine residue, valine 92 residue is replaced with an alanine residue, or glycine 127 residue is replaced with an arginine residue or a combination thereof.

In some embodiments, in the soluble AXL variant polypeptide aspartic acid 87 residue is replaced with a glycine residue or valine 92 residue is replaced with an alanine residue or a combination thereof.

In some embodiments, in the soluble AXL variant polypeptide alanine 72 residue is replaced with a valine residue.

In some embodiments, in the soluble AXL variant polypeptide glycine 32 residue is replaced with a serine residue, aspartic acid 87 residue is replaced with a glycine residue, valine 92 residue is replaced with an alanine residue, glycine 127 residue is replaced with an arginine residue or an alanine 72 residue is replaced with a valine residue or a combination thereof.

In some embodiments, the soluble AXL variant polypeptide comprises amino acid changes relative to the wild-type AXL sequence (SEQ ID NO: 1) at the following positions: (a) glutamic acid 26; (b) valine 79; (c) valine 92; and (d) glycine 127.

In some embodiments, in the soluble AXL variant polypeptide glutamic acid 26 residue is replaced with a glycine residue, valine 79 residue is replaced with a methionine residue, valine 92 residue is replaced with an alanine residue, or glycine 127 residue is replaced with an arginine residue or a combination thereof.

In some embodiments, the soluble AXL variant polypeptide comprises at least an amino acid region selected from the group consisting of amino acid region 19-437, 130-437, 19-132, 21-121, 26-132, 26-121 and 1-437 of the wild-type AXL polypeptide (SEQ ID NO: 1), and wherein one or more amino acid modifications occur in said amino acid region.

In some embodiments, the soluble AXL variant polypeptide comprises amino acid changes relative to the wild-type AXL sequence (SEQ ID NO: 1) at the following positions: (a) glycine 32; (b) aspartic acid 87; (c) alanine 72; and valine 92.

In some embodiments, in the soluble AXL variant polypeptide glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL variant polypeptide is a fusion protein comprising an Fc domain and wherein said AXL variant comprises amino acid changes relative to wild-type AXL sequence (SEQ ID NO:1) at the following positions: (a) glycine 32; (b) aspartic acid 87; (c) alanine 72; and (d) valine 92.

In some embodiments, the soluble AXL variant polypeptide of any of the preceding claims, wherein the soluble AXL polypeptide is a fusion protein comprising an Fc domain and wherein glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL variant polypeptide is a fusion protein comprising an Fc domain and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL variant polypeptide is a fusion protein comprising an Fc domain and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL variant polypeptide is a fusion protein comprising an Fc domain, lacks a functional FN domain, and wherein said AXL variant comprises amino acid changes relative to wild-type AXL sequence (SEQ ID NO:1) at the following positions: (a) glycine 32; (b) aspartic acid 87; (c) alanine 72; and (d) valine 92.

In some embodiments, the soluble AXL variant polypeptide is a fusion protein comprising an Fc domain, lacks a functional FN domain, and wherein glycine 32 is replaced with a serine residue, aspartic acid 87 is replaced with a glycine residue, alanine 72 is replaced with a valine residue, and valine 92 is replaced with an alanine residue, or a combination thereof.

In some embodiments, the soluble AXL variant polypeptide is a fusion protein comprising an Fc domain, lacks a functional FN domain, and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL variant polypeptide is a fusion protein comprising an Fc domain, lacks a functional FN domain, and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL variant polypeptide is a fusion protein comprising an Fc domain, lacks a functional FN domain, lacks an Ig2 domain, and wherein said AXL variant comprises amino acid changes relative to wild-type AXL sequence (SEQ ID NO:1) at the following positions: (a) glycine 32; (b) aspartic acid 87; (c) alanine 72 and (d) valine 92.

In some embodiments, the soluble AXL variant polypeptide is a fusion protein comprising an Fc domain, lacks a functional FN domain, lacks an Ig2 domain and wherein glycine 32 is replaced with a serine residue, aspartic acid 87 is replaced with a glycine residue, alanine 72 is replaced with a valine residue, and valine 92 is replaced with an alanine residue or a combination thereof.

In some embodiments, the soluble AXL variant polypeptide is a fusion protein comprising an Fc domain, lacks a functional FN domain, lacks an Ig2 domain, and wherein said AXL variant comprises amino acid changes relative to wild-type AXL sequence (SEQ ID NO:1) at the following positions: (a) glycine 32; (b) aspartic acid 87; (c) alanine 72; (d) valine 92; and (e) glycine 127.

In some embodiments, the soluble AXL variant polypeptide is a fusion protein comprising an Fc domain, lacks a functional FN domain, lacks an Ig2 domain and wherein glycine 32 is replaced with a serine residue, aspartic acid 87 is replaced with a glycine residue, alanine 72 is replaced with a valine residue, valine 92 is replaced with an alanine residue, and glycine 127 is replaced with an arginine residue or a combination thereof.

In some embodiments, the soluble AXL variant polypeptide of any of the preceding claims, wherein said soluble AXL variant polypeptide has an affinity of at least about $1\times10^{-8}$ M, $1\times10^{-9}$ M, $1\times10^{-10}$ M, $1\times10^{-11}$ M or $1\times10^{-12}$ M for GAS6.

In some embodiments, the soluble AXL variant polypeptide exhibits an affinity to GAS6 that is at least about 5-fold stronger, at least about 10-fold stronger or at least about 20-fold stronger than the affinity of the wild-type AXL polypeptide.

In some embodiments, the soluble AXL variant polypeptide comprises one or more (GLY)$_4$SER (SEQ ID NO:10) units. In some embodiments, the linker comprises 1, 2, 3 or 5 (GLY)$_4$SER (SEQ ID NO:10) units.

In some embodiments, the soluble AXL variant polypeptide inhibits binding between wild-type AXL, MER and/or Tyro3 polypeptide and a GAS6 protein in vivo or in vitro.

In some embodiments, the soluble AXL variant polypeptide is a fusion polypeptide comprising an Fc domain.

In some embodiments, the present invention provides a pharmaceutical composition comprising a therapeutically effective amount of one or more soluble AXL, MER or Tyro3 variant polypeptides.

In some embodiments, the pharmaceutical composition further comprises at least one cytotoxic agent or a pharmaceutically acceptable excipient or a combination thereof.

In some embodiments, the present invention also provides methods of treating, reducing, or preventing the metastasis or invasion of a tumor in a mammalian patient, the method comprising: administering to said patient an effective dose of the inhibitor agent of the present invention. In some embodiments, the inhibitor agent is an AXL, MER or Tyro3 variant polypeptide of any of the preceding claims.

In some embodiments, the tumor for treatment is a tumor selected from the group consisting of an ovarian tumor, a breast tumor, a lung tumor, a liver tumor, a colon tumor, a gallbladder tumor, a pancreatic tumor, a prostate tumor, and glioblastoma.

DEFINITIONS

Figure 1:
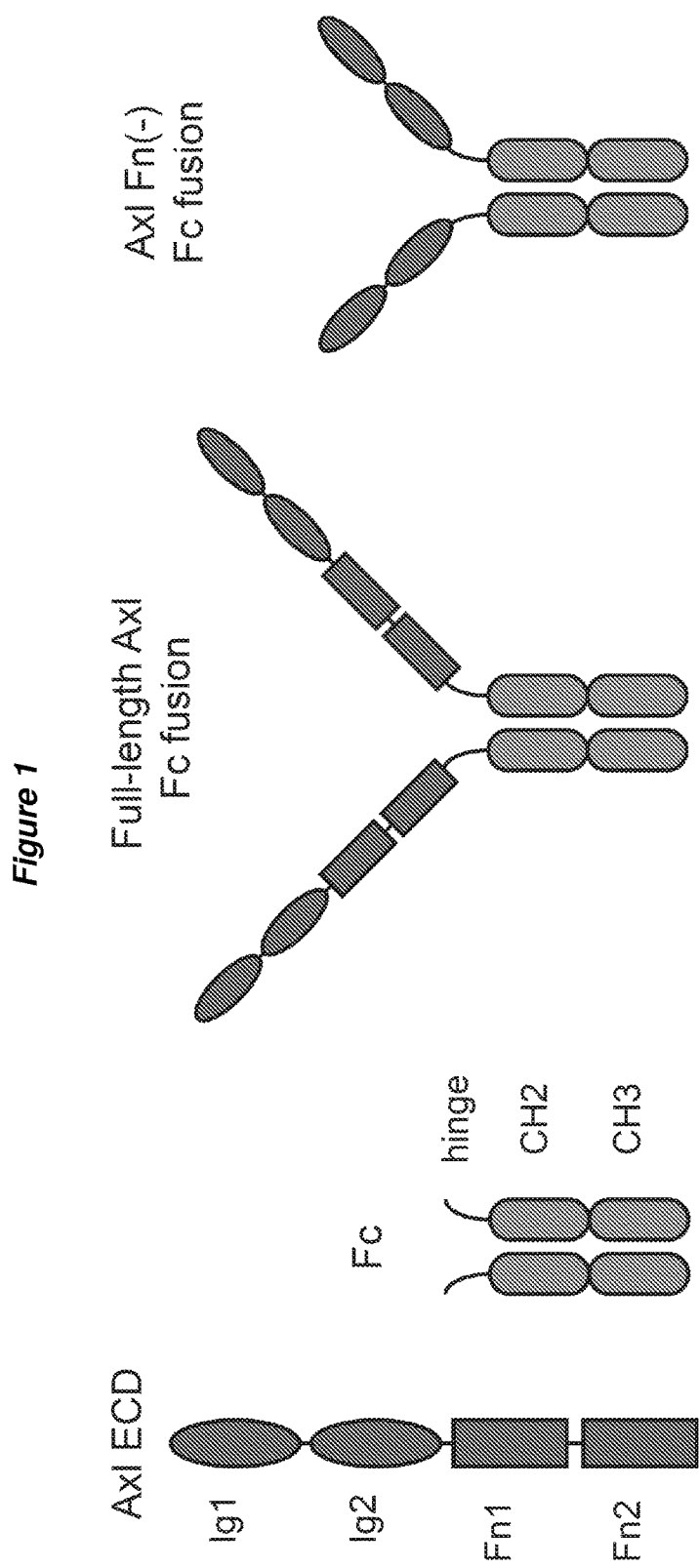
FIG. 1. Describes the four domains of AXL and some embodiments of the various combinations of AXL-Fc constructs that have been made and tested.
Figure 2:
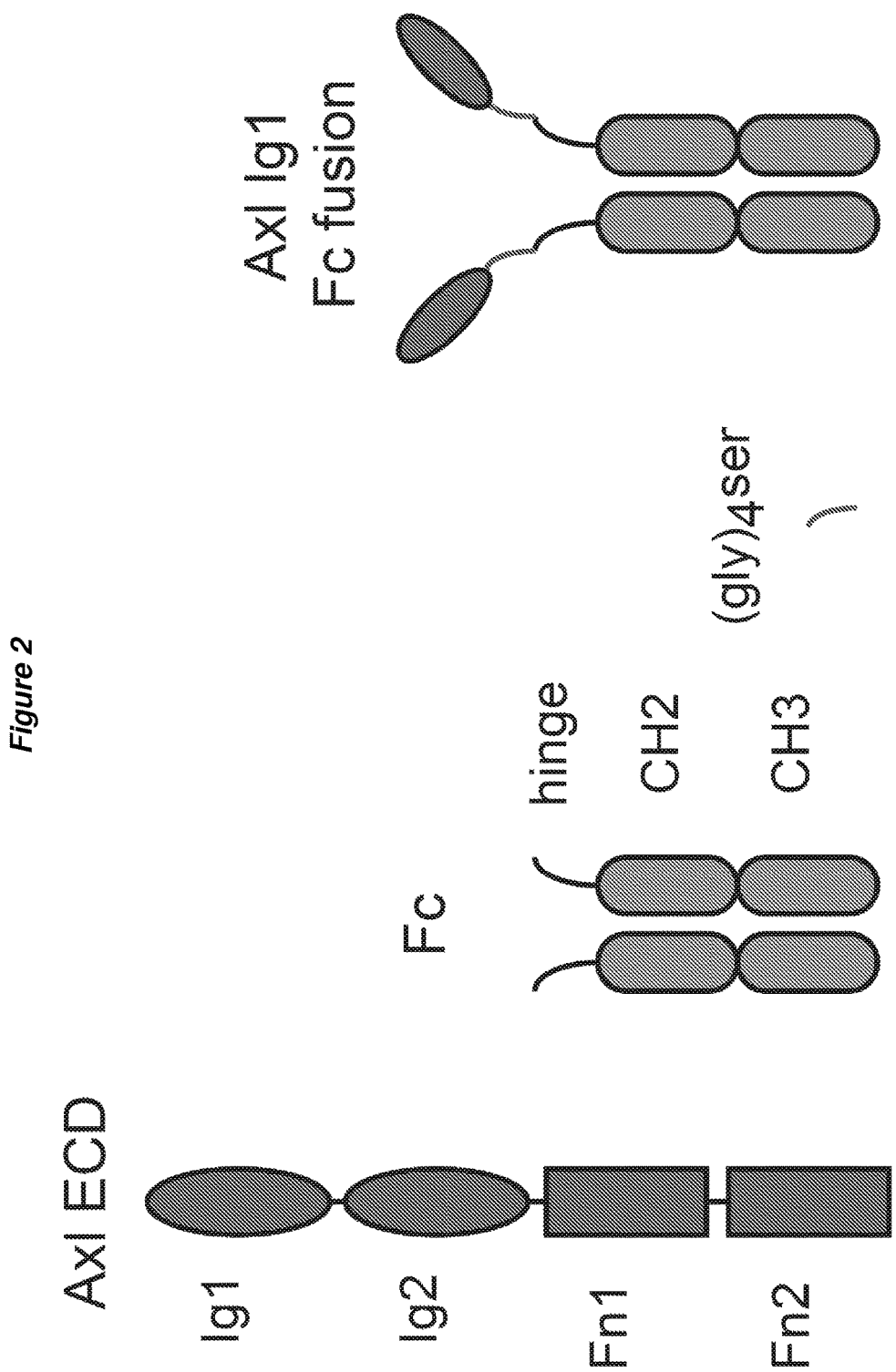
FIG. 2. Describes some embodiments of the various combinations of monovalent AXL-Fc constructs.

In the description that follows, a number of terms conventionally used in the field of cell culture are utilized extensively. In order to provide a clear and consistent understanding of the specification and claims, and the scope to be given to such terms, the following definitions are provided.

"Inhibitors," "activators," and "modulators" of AXL on metastatic cells or its ligand GAS6 are used to refer to inhibitory, activating, or modulating molecules, respectively, identified using in vitro and in vivo assays for receptor or ligand binding or signaling, e.g., ligands, receptors, agonists, antagonists, and their homologs and mimetics.

The terms "polypeptide," "peptide" and "protein" are used interchangeably herein to refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms "antibody" and "antibodies" are used interchangeably herein and refer to a polypeptide capable of interacting with and/or binding to another molecule, often referred to as an antigen. Antibodies can include, for example "antigen-binding polypeptides" or "target-molecule binding polypeptides." Antigens of the present invention can include for example any polypeptides described in the present invention.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. All single letters used in the present invention to represent amino acids are used according to recognized amino acid symbols routinely used in the field, e.g., A means Alanine, C means Cysteine, etc. An amino acid is represented by a single letter before and after the relevant position to reflect the change from original amino acid (before the position) to changed amino acid (after position). For example, A19T means that amino acid alanine at position 19 is changed to threonine.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer, including without limitation, adenocarcinoma of the ovary or prostate, breast cancer, glioblastoma, etc., including those who have undergone or are candidates for resection (surgery) to remove cancerous tissue. Subjects may be human, but also include other mammals, particularly those mammals useful as laboratory models for human disease, e.g. mouse, rat, etc.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, ovarian cancer, glioblastoma, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body. Therefore, the present invention contemplates a method of determining the risk of further growth of one or more cancerous tumors in an organ or body part which is not directly connected to the organ of the original cancerous tumor and/or any steps in a process leading up to that growth.

Depending on the nature of the cancer, an appropriate patient sample is obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques.

The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of any metastatic tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may directly decrease the metastasis of tumor cells.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with neoplasia, e.g., tumor or cancer. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

According to the present invention, the first therapeutic can be any suitable therapeutic agent, e.g., cytotoxic agents. One exemplary class of cytotoxic agents are chemotherapeutic agents, e.g., they can be combined with treatment to inhibit AXL or GAS6 signaling. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate. For ovarian cancer treatment, a preferred chemotherapeutic agent with which an AXL or GAS6 signaling inhibitor can be combined is paclitaxel (Taxol™).

Other combination therapies are radiation, surgery, and hormone deprivation (Kwon et al., Proc. Natl. Acad. Sci U.S.A., 96: 15074-9, 1999). Angiogenesis inhibitors can also be combined with the methods of the invention.

"Concomitant administration" of a known cancer therapeutic drug with a pharmaceutical composition of the present invention means administration of the drug and AXL inhibitor at such time that both the known drug and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTION

AXL, MER and Tyro3 are the three receptor protein tyrosine kinases whose ligand is GAS6. As such, the present invention is based in part on the discovery of inhibitor agents that inhibit and/or antagonize the interaction of the wild-type AXL, MER and/or Tyro3 receptor with the GAS6 ligand.

According to the present invention, such an inhibitor agent can be selected from (a) an inhibitor of AXL, MER and/or Tyro3 activity, (b) an inhibitor of GAS6 activity and (c) an inhibitor of AXL, MER and/or Tyro3-GAS6 interaction, wherein the inhibitor agent is capable of binding to GAS6 with increased affinity compared to wild-type AXL, MER and/or Tyro3.

In some embodiments, the inhibitor agent binds to two or more epitopes on a single GAS6 molecule. The two or more epitopes can include at least one of the major and/or minor AXL, MER and/or Tyro3 binding site on GAS6. In some embodiments, the epitopes are separate or distinct epitopes. In some embodiments the epitopes overlap. In some embodiments, the epitopes do not overlap. In some embodiments, the epitopes are adjacent. In some embodiments, the epitopes are not adjacent. In some embodiments, the epitopes include the major and/or minor AXL, MER and/or Tyro3 binding site on GAS6. These GAS6 epitopes of the present invention, and to which the inhibitor agents of the present invention bind, can be located on one or more GAS6 molecules. In some embodiments, the epitopes are located on a single GAS6 molecule.

In some embodiments, the inhibitor agent is capable of binding to the major and/or minor AXL, MER and/or Tyro3 binding sites on a single GAS6. In some embodiments, the inhibitor agent is capable of binding the major AXL, MER and/or Tyro3 binding site of GAS6 and one or more additional GAS6 epitopes. In other embodiments, the inhibitor agent is capable of binding to the AXL, MER and/or Tyro3 minor binding site on GAS6 and one or more additional epitopes. In some other embodiments, the inhibitor agent is capable of binding two or more distinct epitopes on GAS6. The additional GAS6 epitopes can include any epitopes on GAS6 which lead to increased affinity and/or increased avidity of the inhibitor agent binding to GAS6 as compared to wild-type AXL, MER and/or Tyro3. In some embodiments, the AXL, MER and/or Tyro3 variant polypeptides of the present invention bind two epitopes on a single GAS6 molecule. In some embodiments, the two epitopes are the major and minor AXL, MER and/or Tyro3 binding sites.

According to the invention, GAS6 receptors include AXL, MER and Tyro3. The inhibitor agents of the present invention can also in some embodiments antagonize the major and/or minor GAS6/receptor interaction. In some embodiments, the inhibitor agent is capable of antagonizing the major and/or minor GAS6/receptor binding interaction. In other embodiments, the inhibitor agent is capable of antagonizing the major GAS6/receptor binding interaction (e.g., interfering with and/or inhibiting the major GAS6/receptor binding interaction). In some embodiments, the inhibitor agent is capable of antagonizing the minor GAS6/receptor binding interaction (e.g., interfering with and/or inhibiting the minor GAS6/receptor binding interaction).

Inhibitor agents can also include for example protein scaffolds (i.e., smaller proteins that are capable of achieving comparable affinity and specificity using molecular structures that can be for example one-tenth the size of full antibodies).

The inhibitor agents can also include non-antibody polypeptides. In some embodiments, the inhibitor agent is a non-antibody polypeptide. In some embodiments, the non-antibody polypeptide can include but is not limited to peptibodies, darpins, avimers, adnectins, anticalins, affibodies, maxibodies, or other protein structural scaffold, or a combination thereof.

In some embodiments the inhibitor agent provided by the present invention is an AXL, MER and/or Tyro3 variant polypeptide, e.g., an AXL, MER and/or Tyro3 variant polypeptide that has a binding activity to GAS6 that is substantially equal to or better than the binding activity of a wild-type AXL, MER and/or Tyro3 polypeptide. In some embodiments of the present invention, the AXL, MER and/or Tyro3 variant polypeptides are utilized as therapeutic agents.

The AXL protein, with reference to the native sequence of SEQ ID NO: 1, comprises an immunoglobulin (Ig)-like domain from residues 27-128, a second Ig-like domain from residues 139-222, fibronectin type 3 domains from residues 225-332 and 333-427, intracellular domain from residues 473-894 including tyrosine kinase domain. The tyrosine residues at 779, 821 and 866 become autophosphorylated upon receptor dimerization and serve as docking sites for intracellular signaling molecules. The native cleavage site to release the soluble form of the polypeptide lies at residues 437-451.

For the purposes of the invention, a soluble form of AXL (sAXL) is the portion of the polypeptide that is sufficient to bind GAS6 at a recognizable affinity, e.g., high affinity, which normally lies between the signal sequence and the transmembrane domain, i.e. generally from about SEQ ID NO: 1 residue 19-437, but which may comprise or consist essentially of a truncated version of from about residue 19, 25, 30, 35, 40, 45, 50 to about residue 132, 450, 440, 430, 420, 410, 400, 375, 350, to 321, e.g., residue 19-132. According to the methods of the present invention, SEQ ID NO:1 can be used interchangeably with amino acids 8-894 of SEQ ID NO: 1, both of which refer to the wild-type AXL sequence. In some embodiments, a soluble form of AXL lacks the transmembrane domain, and optionally the intracellular domain.

In some embodiments, the inhibitor agent is a soluble AXL variant polypeptide that lacks the AXL transmembrane domain and has at least one mutation relative to wild-type that increases affinity of the AXL polypeptide binding to GAS6 as compared to wild-type GAS6.

The MER protein, with reference to the native SEQ ID NO:2, comprises an immunoglobulin (Ig)-like domain from residues 81-186, a second Ig-like domain from residues 197-273, fibronectin type 3 domains from residues 284-379 and 383-482, intracellular domain from residues 527-999 including tyrosine kinase domain. The tyrosine residues at 749, 753, 754 and 872 become autophosphorylated upon receptor dimerization and serve as docking sites for intracellular signaling molecules.

For the purposes of the invention, a soluble form of MER (sMER) is the portion of the polypeptide that is sufficient to bind GAS6 at a recognizable affinity, e.g., high affinity, which normally lies between the signal sequence and the transmembrane domain, i.e. generally from about SEQ ID NO: 2 residue 21-526, but which may comprise or consist essentially of a truncated version In some embodiments, a soluble form of MER lacks the transmembrane domain (i.e., generally from about SEQ ID NO: 2 residue 506-526), and optionally the intracellular domain (i.e., generally from about SEQ ID NO: 2 residue 527-999).

In some embodiments, the inhibitor agent is a soluble MER variant polypeptide wherein said MER polypeptide lacks the MER transmembrane domain and has at least one mutation relative to wild-type that increases affinity of the MER polypeptide binding to GAS6 as compared to wild-type MER.

The Tyro3 protein, with reference to the native SEQ ID NO:3, comprises an immunoglobulin (Ig)-like domain from residues 41-128, a second Ig-like domain from residues 139-220, fibronectin type 3 domains from residues 225-317 and 322-413, intracellular domain from residues 451-890 including tyrosine kinase domain. The tyrosine residues at 681, 685, 686 and 804 become autophosphorylated upon receptor dimerization and serve as docking sites for intracellular signaling molecules.

For the purposes of the invention, a soluble form of Tyro3 (sTyro3) is the portion of the Tyro3 polypeptide that is sufficient to bind GAS6 at a recognizable affinity, e.g., high affinity, which normally lies between the signal sequence and the transmembrane domain, i.e. generally from about SEQ ID NO: 3 residue 41-450, but which may comprise or consist essentially of a truncated version In some embodiments, a soluble form of AXL lacks the transmembrane domain (i.e., generally from about SEQ ID NO: 3 residue 430-450), and optionally the intracellular domain (i.e., generally from about SEQ ID NO: 3 residue 451-890).

In some embodiments, the inhibitor agent is a soluble Tyro3 variant polypeptide wherein said Tyro3 polypeptide lacks the Tyro3 transmembrane domain and has at least one mutation relative to wild-type Tyro3 that increases affinity of the Tyro3 polypeptide binding to GAS6 as compared to wild-type Tyro3.

In some embodiments, the AXL, MET or Tyro3 variant polypeptide lacks the AXL, MET or Tyro3 transmembrane domain and is a soluble variant polypeptide, e.g., sAXL, sMER or sTyro3 variant polypeptide.

In some embodiments, the AXL, MER or Tyro3 variant polypeptide lacks the AXL, MER or Tyro3 intracellular domain.

In some embodiments, the inhibitor agent of the present invention inhibits binding between a wild-type AXL, MER and/or Tyro3 polypeptide and a GAS6 protein in vivo or in vitro. In some embodiments, the AXL, MER or Tyro3 variant polypeptide inhibits binding between a wild-type AXL, MER and/or Tyro3 polypeptide and a GAS6 protein in vivo or in vitro.

The inhibitor agents of the present invention can also exhibit an enhanced or better pharmacokinetic profile. In some embodiments, the enhanced or better pharmacokinetic profile includes for example but is not limited to a better absorption profile, better distribution profile, better metabolism profile, better excretion profile, better liberation profile, increased half-life, decrease half-life, faster rate of action, longer duration of effect as compared to AXL, MER and/or Tyro3 wild-type polypeptides which do not lack a transmembrane domain. One of skill in the art would understand preferred pharmacokinetic profile parameters for particular needs including for example treatment regimens, and how to appropriately implement such parameters in treatment regimens.

The wild-type AXL, MER and Tyro3 all contain two fibronectin domains. In some embodiments, the AXL, MER and Tyro3 polypeptides of the invention lack a functional fibronectin (FN) domain. Lacks or lacking a functional fibronectin domain can include but is not limited to deletion of one or both fibronectin domains and/or introducing mutations that inhibit, reduce or remove the functionality of one or both fibronectin domains, where such mutations can include for example but are not limited to substitution, deletion and insertion mutations. In some embodiments, the polypeptides of the invention have fibronectin 1 (FN1) deleted, fibronectin 2 (FN2) deleted, or FN1 and FN 2 both deleted. In some embodiments, the polypeptides of the invention have portions of FN1 mutated and/or deleted, FN2 mutated and/or deleted, or FN1 and FN2 mutated and/or deleted.

In some embodiments, the AXL, MER or Tyro3 variant polypeptide lacks a functional AXL, MER or Tyro3 fibronectin (FN) domain. In some embodiments, the AXL, MER or Tyro3 variant polypeptide exhibits increased affinity of the polypeptide binding to GAS6 as compared to wild-type AXL, MER and/or Tyro3. In some embodiments, the AXL, MER or Tyro3 variant polypeptide lacks a functional fibronectin (FN) domain also exhibits increased affinity of the polypeptide binding to GAS6 as compared to wild-type AXL, MER and/or Tyro3.

In some embodiments, the lack of a functional fibronectin domain results in increased affinity of the AXL, MER or Tyro3 polypeptide binding to GAS6. In some embodiments, the lack of a functional fibronectin domain results in an enhanced or better pharmacokinetic profile, including for example but not limited to a better absorption profile, better distribution profile, better metabolism profile, better excretion profile, better liberation profile, increased half-life, decreased half-life, faster rate of action, longer duration of effect as compared to other wild-type polypeptides or other polypeptides which do not lack a functional fibronectin domain. One of skill in the art would understand preferred pharmacokinetic profile parameters for particular needs including for example treatment regimens, and how to appropriately implement such parameters in treatment regimens.

In some embodiments, the AXL, MER or Tyro3 variant polypeptide lacks the transmembrane domain and has more than one Ig1 domain and exhibits increased affinity of the AXL, MER or Tyro3 polypeptide binding to GAS6 as compared to wild-type AXL, MER and/or Tyro3. In some embodiments, the AXL, MER or Tyro3 polypeptide has two Ig1 domains. In some embodiments, the AXL, MER or Tyro3 polypeptide has three Ig1 domains. In some embodiments, the AXL, MER or Tyro3 polypeptide has more than one Ig1 domain and/or more than one Ig2 domain. In some embodiments, the AXL, MER or Tyro3 polypeptide has two Ig2 domains. In some embodiments, the AXL, MER or Tyro3 polypeptide has two Ig1 domains and 2 Ig2 domains. In some embodiments, the AXL, MER or Tyro3 polypeptide includes for example but is not limited to one of the following Ig domain configurations, as well as any combinations or variations thereof:

Ig1
Ig1-Ig2
Ig1-Ig1
Ig1-Ig1-Ig1
Ig1-Ig2-Ig1
Ig1-Ig2-Ig1-Ig2

In some embodiments, the AXL, MER or Tyro3 polypeptide also lacks the AXL, MER or Tyro3 transmembrane domain and/or exhibits increased affinity of the AXL, MER or Tyro3 polypeptide binding to GAS6. In some embodiments, the AXL, MER or Tyro3 variant polypeptide lacks the transmembrane domain, has more than one Ig1 domain, has more than one Ig2 domain and exhibits increased affinity of the AXL, MER or Tyro3 polypeptide binding to GAS6 as compared to wild-type AXL, MER and/or Tyro3.

In some embodiments, the AXL, MER or Tyro3 has the immunoglobulin domains connected directly to one another. In some embodiments, the AXL, MER or Tyro3 has the immunoglobulin domains connected indirectly, e.g., through a linker molecule including for example any amino acid linker known in the art.

In some embodiments, the one or more AXL, MER or Tyro3 Ig1 and/or 1 or more AXL, MER or Tyro3 Ig2 domains result in an enhanced or better pharmacokinetic profile, including for example but not limited to a better absorption profile, better distribution profile, better metabolism profile, better excretion profile, better liberation profile, increased half-life, decreased half-life, faster rate of action, longer duration of effect as compared to other wild-type polypeptides or other polypeptides which do not lack a functional fibronectin domain. One of skill in the art would understand preferred pharmacokinetic profile parameters for particular needs including for example treatment regimens, and how to appropriately implement such parameters in treatment regimens.

In some embodiments, the AXL, MER or Tyro3 variant polypeptide lacks the AXL, MER or Tyro3 transmembrane domain and is capable of binding two or more epitopes on a single GAS6. In some embodiments, the AXL, MER or Tyro3 variant polypeptide lacks the AXL, MER or Tyro3 transmembrane domain and is capable of binding both the major and minor AXL, MER and/or Tyro3 binding sites on a single GAS6. In some embodiments, the binding of both the major and minor AXL, MER and/or Tyro3 binding is simultaneous. In some embodiments, the binding of both the major and minor AXL, MER and/or Tyro3 binding sites is simultaneous on a single GAS6.

The present invention also provides AXL, MER or Tyro3 variant polypeptides that do not bind two epitopes on a single GAS6 molecule. The present invention also provides AXL, MER or Tyro3 variant polypeptides that do not bind two epitopes on a single GAS6 molecule simultaneously. In some embodiments, the AXL, MER and/or Tyro3 variant polypeptide is not capable of binding two epitopes on a single GAS6, this includes for example monomeric AXL, MER and/or Tyro3 variant polypeptides. In some embodiments, the monomeric AXL, MER or Tyro3 variant polypeptide comprises one Ig1 domain. In some embodiments, the monomeric AXL, MER and/or Tyro3 variant polypeptide is an Fc fusion polypeptide that does not bind to more than one site on a singe Gas6 molecule simultaneously. In some embodiments, the monomeric AXL, MER and/or Tyro3 variant polypeptide that is not capable of binding two epitopes on a single GAS6 comprises two AXL, MER and/or Tyro3 variant polypeptides each of which are not capable of binding two epitopes on a single GAS6 simultaneously. In some embodiments, the monomeric AXL, MER and/or Tyro3 variant polypeptide that is not capable of simultaneously binding two epitopes on a single GAS6 has one Ig1 domain. In some embodiments, the monomeric AXL, MER and/or Tyro3 variant polypeptide that is not capable of simultaneously binding two epitopes on a single GAS6 has an altered half-life when compared to AXL, MER and/or Tyro3 variant polypeptides that are capable of binding two epitopes on a single GAS6. In some embodiments, the polypeptide has one Ig1 domain and lacks a functional Ig2 domain. In some embodiments, the Ig1 domain comprises amino acids 1-131 of AXL (SEQ ID NO:1; or in some embodiments 8-138 of SEQ ID NO:1). In some embodiments, the polypeptide is a soluble AXL, MER or Tyro3 variant polypeptide, wherein said soluble AXL, MER or Tyro3 variant polypeptide lacks the AXL, MER or Tyro3 transmembrane domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3. In some embodiments, the polypeptide of any of the preceding claims, wherein the polypeptide is a soluble AXL, MER or Tyro3 variant polypeptide, wherein said soluble AXL, MER or Tyro3 variant polypeptide lacks the AXL, MER or Tyro3 transmembrane domain, lacks a functional fibronectin (FN) domain, has one Ig1 domain, lacks a functional Ig2 domain and wherein said AXL, MER or Tyro3 variant polypeptide exhibits increased affinity of the AXL, MER or Tyro3 variant polypeptide binding to GAS6 compared to wild-type AXL, MER or Tyro3.

The wild-type AXL, MER and Tyro3 all contain an Ig2 domain. In some embodiments, the AXL, MER and Tyro3 polypeptides of the invention lack a functional Ig2 domain. Lacks or lacking a functional Ig2 domain can include but is not limited to deletion of the Ig2 domain and/or introduction of mutations that inhibit, reduce or remove the functionality of the Ig2 domain, where such mutations can include for example but are not limited to substitution, deletion and insertion mutations. In some embodiments, the polypeptides of the invention lack a functional Ig2 domain. In some embodiments, the polypeptides of the invention lack a functional Ig2 domain and have a wild-type AXL, MER and/or Tyro3 Ig1 domain. In some embodiments, the polypeptides of the invention lack a functional Ig2 domain and have one or more mutations in the Ig1 domain relative to the wild-type AXL, MER and/or Tyro3 Ig1 domain.

In some embodiments, the AXL, MER and/or Tyro3 variant polypeptide includes a linker. A wide variety of linkers are known in the art and any known linker can be employed with the methods of the present invention. In some embodiments, the AXL, MER or Tyro3 variant polypeptide includes one or more linkers or linker units. In some embodiments, the linker is an amino acid linker, including an amino acid sequence of 2, 3, 4 or 5 amino acids which are different that the wild-type AXL, MER and/or Tyro3 sequences. In some embodiments, the linker has 1, 2, 3, 4, 5, 6, 7, 8, 9, 10 or more units. In some embodiments, the linker is $(GLY)_4SER$ (SEQ ID NO:10). In some embodiments, the linker has 1, 2, 3, 4, 5, 6, 7, 8, 9, 10 or more $(GLY)_4SER$ (SEQ ID NO:10) units. In some embodiments, the linker has 1, 2, 3 or 5 $(GLY)_4SER$ (SEQ ID NO:10) units. In some embodiments, the linkers are between the AXL, MER or Tyro3 variant polypeptide and the Fc portion of a fusion polypeptide. In some embodiments, the linkers are between the AXL, MER or Tyro3 variant polypeptide and the Fc portion of a fusion polypeptide and the AXL, MER or Tyro3 variant polypeptide lacks a functional fibronectin domain.

In some embodiments, AXL, MER and/or Tyro3 variant polypeptides of the present invention also include one or more amino acid modifications within the soluble form of wild-type AXL, MER and/or Tyro3, e.g., one or more amino acid modifications that increase its affinity for GAS6. According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids. In still some other embodiments, amino acid modifications include at least 1, 2, 3, 4, 5, or 6 or 10 amino acid mutations or changes.

In some exemplary embodiments, one or more amino acid modifications can be used to alter properties of the soluble form of AXL, MER and/or Tyro3 e.g., affecting the stability, binding activity and/or specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

In some embodiments, AXL variant polypeptides of the present invention include one or more amino acid modifications within one or more regions of residue 18 to 130, residue 10 to 135, residue 15 to 45, residue 60 to 65, residue 70 to 80, residue 85 to 90, residue 91 to 99, residue 104 to 110, residue 111 to 120, residue 125 to 130, residue 19 to 437, residue 130 to 437, residue 19 to 132, residue 21 to 132, residue 21 to 121, residue 26 to 132, or residue 26 to 121 of wild-type AXL (SEQ ID NO: 1). In some other embodiments, AXL variant polypeptides of the present invention include one or more amino acid modifications within one or more regions of residue 20 to 130, residue 37 to 124 or residue 141 to 212 of wild-type AXL (SEQ ID NO: 1). In yet some other embodiments, AXL polypeptide variants of the present invention include one or more amino acid modifications at one or more positions of position 19, 23, 26, 27, 32, 33, 38, 44, 61, 65, 72, 74, 78, 79, 86, 87, 88, 90, 92, 97, 98, 105, 109, 112, 113, 116, 118, 127, or 129 of wild-type AXL (SEQ ID NO: 1).

In yet some other embodiments, AXL polypeptide variants of the present invention include one or more amino acid modifications including without any limitation 1) A19T, 2) T23M, 3) E26G, 4) E27G or E27K, 5) G32S, 6) N33S, 7) T38I, 8) T44A, 9) H61Y, 10) D65N, 11) A72V, 12) S74N, 13) Q78E, 14) V79M, 15) Q86R, 16) D87G, 17) D88N, 18) I90M or I90V, 19) V92A, V92G or V92D, 20) I97R, 21) T98A or T98P, 22) T105M, 23) Q109R, 24) V112A, 25) F113L, 26) H116R, 27) T118A, 28) G127R or G127E, and 29) E129K and a combination thereof.

In yet some other embodiments, AXL variant polypeptides of the present invention include one or more amino acid modifications at position 32, 87, 92, or 127 of wild-type AXL (SEQ ID NO: 1) or a combination thereof, e.g., G32S; D87G; V92A and/or G127R. In yet some other embodiments, AXL polypeptide variants of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, AXL variant polypeptides of the present invention include one or more amino acid modifications at position 32, 87, 92, 127 and/or 72 of wild-type AXL (SEQ ID NO: 1) or a combination thereof, e.g., G32S; D87G; V92A; G127R and/or A72V. In yet some other embodiments, AXL variant polypeptides of the present invention include one or more amino acid modifications at position 87, 92 and/or 127 of wild-type AXL (SEQ ID NO: 1) or a combination thereof, e.g., D87G; V92A; and/or G127R. In yet some other embodiments, AXL variant polypeptides of the present invention include one or more amino acid modifications at position 32, 92, and/or 127 of wild-type AXL (SEQ ID NO: 1) or a combination thereof, e.g., G32S; V92A; and/or G127R. In yet some other embodiments, AXL variant polypeptides of the present invention include one or more amino acid modifications at position 32, 87 and/or 127 of wild-type AXL (SEQ ID NO: 1) or a combination thereof, e.g., G32S; D87G; and/or G127R. In yet some other embodiments, AXL polypeptide variants of the present invention include one or more amino acid modifications at position 32, 87 and/or 92 of wild-type AXL (SEQ ID NO: 1) or a combination thereof, e.g., G32S; D87G; and/or V92A. In yet some other embodiments, AXL variant polypeptides of the present invention include one or more amino acid modifications at position 26, 79, 92, 127 of wild-type AXL (SEQ ID NO: 1) or a combination thereof, e.g., E26G, V79M; V92A and/or G127E. In yet some other embodiments, AXL variant polypeptides of the present invention include one or more amino acid modifications at position 87 and 92 of wild-type AXL (SEQ ID NO: 1) or a combination thereof, e.g., D87G and V92A. In yet some other embodiments, AXL variant polypeptides of the present invention include at least one amino acid modification at position 72 of wild-type AXL (SEQ ID NO: 1), e.g., A72V.

According to the present invention, the inhibitor agent can include but is not limited to a polypeptide, a polypeptide-carrier fusion, a polypeptide-Fc fusion, polypeptide-conjugate, a polypeptide-drug conjugate, an antibody, a bispecific antibody, an antibody-drug conjugate, an antibody fragment, an antibody-related structure, or a combination thereof.

The inhibitor agents of the present invention can include peptides or polypeptides. The peptides and polypeptides of the present invention can include natural and/or synthetic polypeptides. Synthetic polypeptides and methods of making synthetic polypeptides are well known in the art and any known methods for making synthetic polypeptides can be employed with the methods of the present invention. In some embodiments, the inhibitor agent is a natural or synthetic polypeptide. In some embodiments, the inhibitor agent is a natural or synthetic polypeptide-fusion. In some embodiments, the inhibitor agent is a natural or synthetic polypeptide-Fc fusion. In some embodiments the natural or synthetic polypeptide-fusion is a fusion with another protein structural class or scaffold or a natural or synthetic polypeptide-fusion with a polymer or hydrogel or related structure.

According to the present invention, the AXL, MER or Tyro3 variant polypeptides of the present invention can be further modified, e.g., joined to a wide variety of other oligopeptides or proteins for a variety of purposes. For instance, various post-translation or post-expression modifications can be carried out with respect to AXL, MER or Tyro3 variant polypeptides of the present invention. For example, by employing the appropriate coding sequences, one may provide farnesylation or prenylation. In some embodiments, the AXL, MER or Tyro3 variant polypeptides of the present invention can be PEGylated, where the polyethyleneoxy group provides for enhanced lifetime in the blood stream. The AXL, MER or Tyro3 variant polypeptides of the present invention can also be combined with other proteins, such as the Fc of an IgG isotype, which can be complement binding, with a toxin, such as ricin, abrin, diphtheria toxin, or the like, or with specific binding agents that allow targeting to specific moieties on a target cell. The inhibitor agents of the present invention can include polypeptide conjugates and antibody-conjugates. In some embodiments, the inhibitor agent is a polypeptide-conjugate or antibody-conjugate. In some embodiments, the polypeptide conjugate is a drug conjugate. In some embodiments, the peptide or polypeptide conjugate is an antibody-drug conjugates. In some embodiments, the polypeptide conjugate is a polymer conjugate. Polymers of the present invention include but are not limited to PEG, PEG-containing polymers, degradable polymers, biocompatible polymers, hydrogels, as well as other polymer structures that could be conjugated to a polypeptide, and can include combinations thereof.

In some embodiments, the AXL, MER or Tyro3 variant polypeptide of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. In yet some other embodiments, the second polypeptide is part or whole of an albumin protein, e.g., a human serum albumin protein. In some embodiments, the second polypeptide is a protein or peptide that binds to albumin.

In some other embodiments, the second polypeptide is useful for handling the AXL, MER or Tyro3 variant polypeptides, e.g., purification of AXL, MER or Tyro3 variant polypeptides or for increasing stability in vitro or in vivo. For example, AXL, MER or Tyro3 variant polypeptides of the present invention can be combined with parts of the constant domain of immunoglobulins (IgG), resulting in chimeric or fusion polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. EP A 394,827; Traunecker et al., Nature, 331: 84-86, 1988. Fusion proteins having disulfide-linked dimeric structures (due to the IgG) can also be more efficient in binding and neutralizing other molecules, than the monomeric secreted protein or protein fragment alone. Fountoulakis et al., J. Biochem. 270: 3958-3964,1995.

In yet some other embodiments, the second polypeptide is a marker sequence, such as a peptide which facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984.

In still some other embodiments, the second polypeptide is an entity useful for improving the characteristics of AXL, MER or Tyro3 polypeptide variants of the present invention. For instance, a region of additional amino acids, particularly charged amino acids, may be added to the N-terminus of the polypeptide to improve stability and persistence during purification from the host cell or subsequent handling and storage. Also, peptide moieties may be added to the AXL, MER or Tyro3 polypeptide variants of the present invention to facilitate purification and subsequently removed prior to final preparation of the polypeptide. The addition of peptide moieties to facilitate handling of polypeptides are familiar and routine techniques in the art.

In still yet some embodiments, AXL, MER or Tyro3 variant polypeptides of the present invention have a binding activity to GAS6 that is at least equal or better than the wild-type AXL, MER or Tyro3. In some other embodiments, AXL, MER or Tyro3 variant polypeptides of the present invention has a binding activity or affinity to GAS6 that is at least 1-fold, 2-fold, 3-fold, 4-fold, 5-fold, or 6-fold greater than that of the wild-type AXL, MER or Tyro3. In some other embodiments, AXL, MER or Tyro3 polypeptide variant of the present invention has a binding activity or affinity to GAS6 of at least about $1\times10^{-6}$, $1\times10^{-7}$, $1\times10^{-8}$ or $1\times10^{-9}$ M $1\times10^{-10}$M, $1\times10^{-11}$M or $1\times10^{-12}$M. In yet some other embodiments, sAXL polypeptides of the present invention is capable of inhibiting, inhibit or compete with wild-type AXL binding to GAS6 either in vivo, in vitro or both. In yet some other embodiments, sAXL polypeptides of the present invention inhibit or compete with the binding of AXL S6-1, AXL S6-2, and/or AXL S6-5 (as described in WO2011/091305). In yet some other embodiments, sAXL polypeptides of the present invention inhibit or compete with the binding of any sAXL variant as described in WO2011/091305.

The inhibitor agents of the present invention bind to GAS6 with increased affinity. In some embodiments, the AXL, MER or Tyro3 variant polypeptide exhibits increased affinity of the AXL, MER or Tyro3 polypeptide binding to GAS6 as compared to wild-type AXL, MER or Tyro3. In some embodiments, AXL, MER or Tyro3 variant polypeptide exhibits an affinity to GAS6 that is at least about 5-fold stronger, at least about 10-fold stronger or at least about 20-fold stronger, 50-fold stronger, 100-fold stronger or at least 200-fold stronger, etc. than the affinity of the wild-type AXL, MER or Tyro3 polypeptide. In some embodiments, the soluble AXL has a about a 115-fold stronger affinity to GAS6 than the affinity of the wild-type AXL polypeptide.

The ability of a molecule to bind to GAS6 can be determined, for example, by the ability of the putative ligand to bind to GAS6 coated on an assay plate. In one embodiment, the binding activity of AXL, MER or Tyro3 variant polypeptides of the present invention to a GAS6 can be assayed by either immobilizing the ligand, e.g., GAS6 or the AXL, MER or Tyro3 variant polypeptides. For example, the assay can include immobilizing GAS6 fused to a His tag onto Ni-activated NTA resin beads. Agents can be added in an appropriate buffer and the beads incubated for a period of time at a given temperature. After washes to remove unbound material, the bound protein can be released with, for example, SDS, buffers with a high pH, and the like and analyzed.

In still yet other embodiments, AXL, MER or Tyro3 variant polypeptides of the present invention has a better thermal stability than the thermal stability of a wild-type AXL. In some embodiments, the melting temperature of AXL, MER or Tyro3 variant polypeptides of the present invention is at least 5° C., 10° C., 15° C., or 20° C. higher than the melting temperature of a wild-type AXL.

According to the present invention, AXL, MER or Tyro3 variant polypeptides of the present invention can also include one or more modifications that do not alter primary sequences of the AXL, MER or Tyro3 variant polypeptides of the present invention. For example, such modifications can include chemical derivatization of polypeptides, e.g., acetylation, amidation, carboxylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, AXL, MER or Tyro3 polypeptide variants of the present invention include AXL, MER or Tyro3 variant polypeptides having phosphorylated amino acid residues, e.g. phosphotyrosine, phosphoserine, or phosphothreonine.

In some other embodiments, AXL, MER or Tyro3 variant polypeptides of the present invention include AXL, MER or Tyro3 variant polypeptides further modified to improve their resistance to proteolytic degradation or to optimize solubility properties or to render them more suitable as a therapeutic agent. For example, AXL, MER or Tyro3 polypeptide variants of the present invention further include analogs of AXL, MER or Tyro3 variant polypeptides containing residues other than naturally occurring L-amino acids, e.g. D-amino acids or non-naturally occurring synthetic amino acids. D-amino acids may be substituted for some or all of the amino acid residues.

In yet some other embodiments, AXL, MER or Tyro3 variant polypeptides of the present invention include at least two same or different AXL, MER or Tyro3 variant polypeptides linked covalently or non-covalently. For example, in some embodiments, AXL, MER or Tyro3 polypeptide variants of the present invention include two, three, four, five, or six same or different AXL, MER or Tyro3 variant polypeptides linked covalently, e.g., so that they will have the appropriate size, but avoiding unwanted aggregation.

According to the present invention, AXL, MER or Tyro3 variant polypeptides of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The AXL, MER or Tyro3 variant polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The AXL, MER or Tyro3 variant polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

In some embodiments, the present invention provides expression vectors for in vitro or in vivo expression of one or more AXL, MER and/or Tyro3 polypeptide variants of the present invention, either constitutively or under one or more regulatory elements. In some embodiments, the present invention provides a cell population comprising one or more expression vectors for expressing AXL, MER and/or Tyro3 polypeptide variants of the present invention, either constitutively or under one or more regulatory elements.

According to another aspect of the invention, it provides isolated antibodies or fragments thereof which specifically bind to a GAS6 protein. GAS6 (growth arrest-specific 6) belongs structurally to the family of plasma vitamin K-dependent proteins. GAS6 has a high structural homology with the natural anticoagulant protein S, sharing the same modular composition and having 40% sequence identity. GAS6 has growth factor-like properties through its interaction with receptor tyrosine kinases of the TAM family; Tyro3, AXL and MER. Human GAS6 is a 678 amino acid protein that consists of a gamma-carboxyglutamate (Gla)-rich domain that mediates binding to phospholipid membranes, four epidermal growth factor-like domains, and two laminin G-like (LG) domains. The sequence of the transcript variants of human GAS6 may be accessed at Genbank at NM_001143946.1; NM_001143945.1; and NM_000820.2, respectively.

GAS6 employs a unique mechanism of action, interacting through its vitamin K-dependent GLA (gamma-carboxyglutamic acid) module with phosphatidylserine-containing membranes and through its carboxy-terminal LamG domains with the TAM membrane receptors.

According to the present invention, isolated antibodies of the present invention include any isolated antibodies with a recognizable binding specificity against GAS6. In some embodiments, isolated antibodies are partially or fully humanized antibodies. In some other embodiments, isolated antibodies are monoclonal or polyclonal antibodies. In yet some other embodiments, isolated antibodies are chimeric antibodies, e.g., with consistent regions, variable regions and/or CDR3 or a combination thereof from different sources. In yet some other embodiments, isolated antibodies are a combination of various features described herein.

According to the present invention, fragments of the isolated antibodies of the present invention include a polypeptide containing a region of the antibody (either in the context of an antibody scaffold or a non-antibody scaffold) that is sufficient or necessary for a recognizable specific binding of the polypeptide towards GAS6. In some embodiments, fragments of the isolated antibodies of the present invention include variable light chains, variable heavy chains, one or more CDRs of heavy chains or light chains or combinations thereof, e.g., Fab, Fv, etc. In some embodiments, fragments of the isolated antibodies of the present invention include a polypeptide containing a single chain antibody, e.g., ScFv. In yet some embodiments, fragments of the isolated antibodies of the present invention include variable regions only or variable regions in combination with part of Fc region, e.g., CH1 region. In still some embodiments, fragments of the isolated antibodies of the present invention include minibodies, e.g., VL-VH-CH3 or diabodies.

In some embodiments, isolated antibodies of the present invention bind to an epitope comprised in or presented by one or more amino acid regions that interact with AXL, MER and/or Tyro3. In some other embodiments, isolated antibodies of the present invention bind to an epitope comprised in or presented by one or more amino acid regions of GAS6, e.g., L295-T317, E356-P372, R389-N396, D398-A406, E413-H429, and W450-M468 of GAS6.

In yet some other embodiments, isolated antibodies of the present invention bind to an epitope comprised in or presented by one or more amino acid regions, e.g., LRMFSGT-PVIRLRFKRLQPT (SEQ ID NO: 4), EIVGRVTSSGP (SEQ ID NO: 5), RNLVIKVN (SEQ ID NO: 6), DAVMKIAVA (SEQ ID NO: 7), ERGLYHLNLTVGIPFH (SEQ ID NO: 8), and WLNGEDTTIQETVVNRM (SEQ ID NO: 9).

In yet some other embodiments, isolated antibodies of the present invention bind to an epitope comprised in or presented by at least one, two, three, four, five, or six amino acids in a region of L295-T317, E356-P372, R389-N396, D398-A406, E413-H429, and W450-M468 of GAS6. In yet some other embodiments, isolated antibodies of the present invention bind to an epitope comprised in or presented by at least one, two, three, four, five or six amino acids in a region of LRMFSGTPVIRLRFKRLQPT (SEQ ID NO: 4), EIVGRVTSSGP (SEQ ID NO: 5), RNLVIKVN (SEQ ID NO: 6), DAVMKIAVA (SEQ ID NO: 7), ERGLYHLNLTVGIPFH (SEQ ID NO: 8), and WLNGEDTTIQETVVNRM (SEQ ID NO: 9).

In still some other embodiments, isolated antibodies of the present invention is capable of inhibiting, inhibits or competes with the binding between wild-type AXL, MER and/or Tyro3 or AXL, MER and/or Tyro3 polypeptide variants of the present invention and GAS6.

According to the present invention, the AXL, MER or Tyro3 variant polypeptides and isolated antibodies of the present invention can be provided in pharmaceutical compositions suitable for therapeutic use, e.g., for human treatment. In some embodiments, pharmaceutical compositions of the present invention include one or more therapeutic entities of the present invention, e.g., AXL polypeptide variants and/or isolated antibodies against GAS6 or pharmaceutically acceptable salts, esters or solvates thereof or any prodrug thereof. In some other embodiments, pharmaceutical compositions of the present invention include one or more therapeutic entities of the present invention in combination with another cytotoxic agent, e.g., another anti-tumor agent. In yet some other embodiments, pharmaceutical compositions of the present invention include one or more therapeutic entities of the present invention in combination with another pharmaceutically acceptable excipient.

In still some other embodiments, therapeutic entities of the present invention are often administered as pharmaceutical compositions comprising an active therapeutic agent, i.e., and a variety of other pharmaceutically acceptable components. (See Remington's Pharmaceutical Science, 15.sup.th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

According to yet another aspect of the invention, it provides methods for treating, reducing or preventing tumor metastasis or tumor invasion by inhibiting the AXL, MER or Tyro3 signaling pathway and/or GAS6 signaling pathway. In some embodiments, methods of the present invention include inhibiting the activity of AXL, MER, Tyro3 and/or GAS6, or the interaction between AXL, MER and/or Tyro3 and GAS6. For example, the activity of AXL, MER, Tyro3 and/or GAS6 can be inhibited at the gene expression level, mRNA processing level, translation level, post-translation level, protein activation level, etc. In some other examples, the activity of AXL, MER, Tyro3 or GAS6 can be inhibited by small molecules, biological molecules, e.g., polypeptides, polynucleotides, antibodies, antibody drug conjugates, etc. In some other examples, the activity of AXL, MER, Tyro3 or GAS6 can be inhibited by one or more AXL, MER or Tyro3 variant polypeptides or isolated antibodies of the present invention.

In yet other embodiments, methods of the present invention include administering to a subject in need of treatment a therapeutically effective amount or an effective dose of a therapeutic entity (e.g., inhibitor agent) of the present invention, e.g., an inhibitor of AXL, MER and/or Tyro3 activity or GAS6 activity or an inhibitor of interaction between AXL, MER and/or Tyro3 and GAS6. In some embodiments, effective doses of the therapeutic entity of the present invention, e.g. for the treatment of metastatic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

In some embodiments, the dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor metastasis or tumor invasion of ovarian cancer, breast cancer, lung cancer, liver cancer, colon cancer, gallbladder cancer, pancreatic cancer, prostate cancer, and/or glioblastoma.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved. Typically, the response is monitored and repeated dosages are given if there is a recurrence of the cancer.

According to the present invention, compositions for the treatment of metastatic cancer can be administered by parenteral, topical, intravenous, intratumoral, oral, subcutaneous, intraarterial, intracranial, intraperitoneal, intranasal or intramuscular means. The most typical route of administration is intravenous or intratumoral although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. I n general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. An exemplary composition comprises polypeptide at 1 mg/mL, formulated in aqueous buffer consisting of 10 mM Tris, 210 mM sucrose, 51 mM L-arginine, 0.01% polysorbate 20, adjusted to pH 7.4 with HCl or NaOH.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration.

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions (e.g., AXL, MER or Tyro3 variant polypeptides and formulations thereof) of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

According to yet another aspect of the invention, it provides methods for determining the ability of a tumor to undergo tumor invasion and/or metastasis by detecting and/or determining the level of AXL, MER and/or Tyro3 activity or GAS6 activity in a biological sample from a subject of interest. In some embodiment, the level of AXL, MER and/or Tyro3 activity or GAS6 activity is measured by the level of mRNA expression, the level of protein expression, the level of protein activation or any suitable indicator corresponding to the activity of AXL, MER and/or Tyro3 or GAS6 either directly or indirectly. In some embodiments, the level of AXL, MER and/or Tyro3 activity or GAS6 activity in a biological sample is further compared to a predetermined level, e.g., standard level obtained by establishing normal levels or ranges of AXL, MER and/or Tyro3 activity or GAS6 activity based on a population of samples from tumors that do not develop tumor invasion or tumor metastasis or from normal tissues. For example, an increase of AXL, MER and/or Tyro3 activity or GAS6 activity over the predetermined level or standard level is indicative of a predisposition of the tumor to undergo tumor invasion or tumor metastasis.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples will be described to illustrate parts of the invention. It is also understood that the terminology used herein is for the purposes of describing particular embodiments.

EXPERIMENTAL

Example 1—Affinities of Various AXL Fc Constructs

FIG. 1 shows the four domains of AXL and the various combinations of AXL Fc constructs made and tested.

The following AXL Fc constructs were made:
a. Full-length wild-type Fc fusion
b. Full-length AXL peptide 1 Fc fusion
c. AXL peptide 1 Fn(–) Fc fusion (this is the Fn– construct)
d. Full-length AXL peptide 1 Fc fusion with minor GAS6 binding site knocked out
e. AXL peptide 1 Fn(–) Fc fusion, 3× gly4ser linker between Fc and AXL
f. AXL peptide 1 Fn(–) Fc fusion, 5× gly4ser linker between Fc and AXL
g. AXL peptide 1 A72V Fn(–) Fc fusion, 3× gly4ser linker between Fc and AXL The following Table 1 outlines the affinities of the above constructs to GAS6, with wild-type AXL as a comparison.

TABLE 1

| Construct Affinities | | | | |
|---|---|---|---|---|
| AXL clone | Fn domains | Fc | Linker | $K_d$ (pM) |
| Wild-type Ig1 | – | None | None | 32.8 ± 0.63 |
| AXL peptide 1 Ig1 | – | None | None | 2.7 ± 0.05 |
| (a) Wild-type | + | hIgG | None | 9.2 ± 0.17 |
| (b) AXL peptide 1 | + | hIgG | None | 0.4 ± 0.01 |
| (c) AXL peptide 1 | – | hIgG | None | 2.6 ± 0.05 |
| (d) AXL peptide 1 (–) minor site | + | hIgG | None | 2.6 ± 0.10 |
| (e) AXL peptide 1 | – | hIgG | 3× gly4ser (SEQ ID NO: 10) | 1.2 ± 0.03 |
| (f) AXL peptide 1 | – | hIgG | 5× gly4ser (SEQ ID NO: 10) | 1.2 ± 0.03 |
| (g) AXL peptide 1 A72V | – | hIgG | 3× gly4ser (SEQ ID NO: 10) | 0.3 ± 0.00 |

There are several conclusions that can be drawn from the data set in Table 1 above.

Fc-fusion constructs provide enhancements in affinity over the monomeric forms. For example: wild-type AXL Ig1 (monomeric) has a ~33 pM affinity, whereas wild-type Fc fusion has an affinity of ~9 pM and AXL peptide 1 Ig1 (monomeric) has an affinity of ~3 pM, whereas AXL peptide 1-Fc fusion has an affinity of ~0.4 pM Significant affinity improvements for AXL peptide 1 over wild-type AXL. In addition, AXL peptide 1 plus the A72V mutation has a further enhancement in affinity, construct (e) compared to construct (g), over wild-type AXL.

The mechanism of increasing the affinity in the Fc fusion comes from multivalent binding to a single GAS6 molecule. Specifically, one arm of the fusion binds to the major AXL binding site while the other binds the minor. This conclusion was based on the following experimental data:

a. AXL peptide 1 Ig1 (monomer) has the same affinity as the AXL peptide 1 Fn(−) Fc fusion, (c) in the table above. This suggests that simply having two copies of AXL is insufficient for providing affinity improvement.
b. Full-length AXL peptide 1 with the minor binding site removed has the same affinity as the monomer and the Fn(−) fusion. This shows that the minor binding site has a definitive role in the affinity improvements.
c. The Fn(−) constructs are arranged such that the minor binding site is inaccessible to the large GAS6 molecule. The addition of linkers between AXL and the Fc provide additional flexibility and space, and with that a two-fold improvement in affinity is obtained. This further supports the idea that the minor binding site is important.

Overall, Example 1 shows that Fc fusions of the AXL ECD can have improved affinity to GAS6 compared to wild-type AXL. While not being bound by theory, one mechanism underlying this improved affinity is simultaneous binding of one arm of the construct to the major AXL binding site on GAS6 and the other arm to the minor AXL binding site on GAS6.

Example 2—Affinities of Various AXL Fc Constructs

Sequence: AXL peptide 2-Fc. The AXL peptide 2 includes amino acids 1-131 of AXL, has the Ig2 domain deleted and has both the FN domains deleted.

This construct includes amino acids 1-131 of AXL fused to the human IgG1, with a single $Gly_4Ser$ (SEQ ID NO:10) linker connecting the two domains (see FIG. 2). Additionally, constructs can include various mutations in the AXL portion of the molecule, as described by the present invention. For example, embodiments can include having AXL peptide 1 Ig1 Fc fusion or AXL peptide 1 plus A72V.

The affinity of AXL peptide 1 Ig1-Fc to human GAS6 has been measured to be 1.7+/−0.03 pM.

Overall, Example 2 shows that Fc fusions of the AXL Ig1 domain can have improved affinity to GAS6 compared to wild-type AXL.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

What is claimed is:

1. An inhibitor of GAS6, wherein the inhibitor is a soluble AXL variant polypeptide, wherein said soluble AXL variant polypeptide:
   lacks the AXL transmembrane domain,
   lacks a functional fibronectin (FN) domain,
   has an Ig1 domain, and an Ig2 domain,
   comprises a set of amino acid substitutions relative to SEQ ID NO:1 selected from Gly32Ser, Asp87Gly, Val92Ala, and Gly127Arg; or Gly32Ser, Ala72Val, Asp87Gly, Val92Ala, and Gly127Arg,
   comprises an Fc domain linked to the AXL variant polypeptide by a linker comprising from 1 to 5 (GLY)$_4$SER (SEQ ID NO:10) units; and
   wherein said AXL variant polypeptide exhibits increased affinity of binding to GAS6 compared to wild-type AXL (SEQ ID NO:1).

2. The inhibitor of claim 1, in a pharmaceutically acceptable excipient.

3. A method of reducing growth or metastasis of a tumor that expresses GAS6, the method comprising administering to a patient with a tumor that expresses GAS6 an effective dose of the inhibitor of claim 1.

* * * * *